United States Patent [19]

Dereu et al.

[11] Patent Number: 5,492,915
[45] Date of Patent: Feb. 20, 1996

[54] SUBSTITUTED QUINOLYL COMPOUNDS EXHIBITING SELECTIVE LEUKOTRIENE $B_4$ ANTAGONIST ACTIVITY

[75] Inventors: Norbert Dereu, Viry-Chatillon, France; Wolfram Hendel, Leonding, Austria; Richard Labaudiniere, Vitry-sur-Seine, France

[73] Assignee: Rhone-Poulenc Rorer S.A., Antony Cedex, France

[21] Appl. No.: 318,919

[22] Filed: Oct. 6, 1994

Related U.S. Application Data

[62] Division of Ser. No. 966,151, Feb. 17, 1993, Pat. No. 5,366,982.

[30] Foreign Application Priority Data

Jul. 24, 1990 [FR] France ................... 90 09453

[51] Int. Cl.$^6$ ............ A61K 31/47; C07D 215/14; C07D 215/227; C07D 215/38
[52] U.S. Cl. ............ 514/311; 514/312; 514/313; 514/314; 546/155; 546/156; 546/157; 546/159; 546/162; 546/167; 546/169; 546/173; 546/175; 546/176; 546/177; 546/179; 546/180
[58] Field of Search ................... 514/311, 312, 514/313, 314; 546/155, 156, 157, 159, 162, 169, 175, 176, 180, 167, 173, 177, 179

[56] References Cited

PUBLICATIONS

Kaihara et al., Arch. Biochem., Biophys. 110(2), 316–19 (1965).

Primary Examiner—Raymond Henley, III
Assistant Examiner—Phyllis G. Spivack
Attorney, Agent, or Firm—James A. Nicholson; Martin F. Savitzky; Raymond S. Parker, III

[57] ABSTRACT

This invention relates to compounds having selective $LTB_4$ antagonist properties. Therapeutic compositions comprising said compounds and methods for the treatment of disorders involving $LTB_4$ agonist-mediated activity utilizing said compositions wherein the compounds are described by the formula

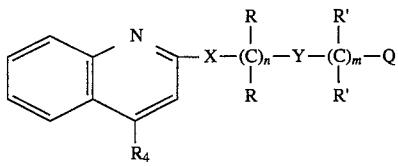

wherein $R_4$, X, R, Y, R', Q, m and n are herein defined, and pharmaceutically acceptable salts thereof.

9 Claims, No Drawings

SUBSTITUTED QUINOLYL COMPOUNDS EXHIBITING SELECTIVE LEUKOTRIENE B₄ ANTAGONIST ACTIVITY

This is a divisional of application Ser. No. 07/966,151 filed on Feb. 17, 1993, now U.S. Pat. No. 5,366,982.

FIELD OF THE INVENTION

The present invention relates to a class of novel compounds useful in the treatment of a variety of diseases that involve undesirable inflammatory or hypersensitivity responses in diverse animal tissues. Approaches to the treatment of these diseases have been as varied as the tissues in which such responses take place, and include the administration of antihistamines, analgesics such as aspirin, topical coal tar as well as others.

A more recent approach to the moderation of inflammatory and hypersensitivity responses has focused on blocking the action of arachidonic acid metabolites (including the prostaglandins), lipoxygenases and the leukotrienes. The leukotrienes (LT) metabolites are formed by oxygenation of a lipoxygenase (5-hydroperoxy-tetraenoic acid (5-HPETE)) which is formed by the specific oxygenation of the C-5 position of arachidonic acid. The first leukotriene formed in the metabolic pathway is the unstable epoxide intermediate leukotriene $A_4$ ($LTA_4$) which is the precursor to the family of peptido-leukotrienes, the first in the pathway being $LTC_4$ which is formed by glutathione addition. $LTC_4$ is transformed subsequently into $LTD_4$ and $LTE_4$ by successive elimination of a glutamyl and glycine residue. The peptido-leukotrienes primarily act on smooth muscle and other cells having contractile capacity, as well as playing a key role in hypersensitivity reactions. In addition, the peptido-leukotrienes are spasmogens, increase vascular permeability, activate airway smooth muscle, stimulate mucous secretion and are involved with the pathogenesis of certain inflammatory diseases such as bronchitis, ectopic and atopic eczema and psoriasis. Leukotrienes appear to be involved in the pathogenesis of asthma such as allergic pulmonary disorders of asthma, hay fever and allergic rhinitis. In addition, $LTC_4$, $LTD_4$ and $LTE_4$ may also decrease blood pressure by an action on the heart, because they reduce myocardial contractility and coronary blood flow.

Another family of leukotrienes, $LTB_4$, is derived from $LTA_4$ by hydrolase-catalyzed addition of water. This 5,12-dihydroxy derivative causes adhesion and chemotactic movement of leukocytes, stimulates aggregation, enzyme release and generation of superoxide in neutrophils. Additionally, LTB4 is a potent chemotactic and chemokinetic agent for eosinophils, macrophages and monocytes, stimulates suppressor T lymphocytes and enhances natural cytotoxic cell activity. $LTB_4$ is also a potent (indirect) bronchoconstrictor but in contrast to the peptido-leukotrienes $C_4$, $D_4$ and $E_4$ does not appreciably stimulate mucous production and induce edema of the airways by increasing vascular permeability.

It has been suggested that compounds antagonizing $LTB_4$ activity may be valuable in the treatment of inflammatory diseases caused by tissue degrading enzymes and reactive chemicals liberated by tissue-infiltrating and aggregating polymorphonuclear leukocytes. Such disease states include inflammatory bowel disease, reperfusion injury, chronic lung diseases, various arthritic conditions, inflammatory conditions associated with asthma (such as late phase hypersensitivity) and psoriasis.

REPORTED DEVELOPMENTS

Compounds reported to have anti-inflammatory properties and/or heterocyclic structures relevant to those within the scope of the present invention are described below.

In the Belgian Patent 724,667 pyridine derivatives of structure:

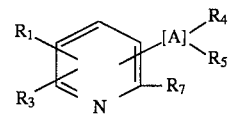

wherein $R_1$ is a hydrogen atom or among others a phenyl, $R_3$ is hydrogen or an alkyl, $R_4$ and $R_5$ are in particular hydrogen, an alkyl or a phenyl, $R_7$ is a radical of structure —$OR_8$ or —$SR_8$ for which $R_8$ is in particular a lower alkyl optionally substituted by a nitro, an amino or a halogen, or a benzyl, and [A] is a heterocyclic or carbocyclic aryl. These products are useful in the area of anti-inflammatory agents.

In U.S. Pat. No. 3,391,146, there are disclosed anti-inflammatory agents of general formula:

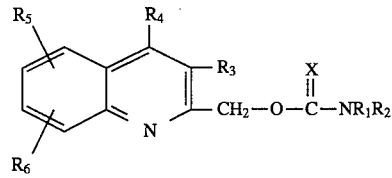

wherein X is O or S, $R_1$ and $R_2$ are among others a lower alkyl, $R_3$, $R_4$, $R_5$ and $R_6$ are among others alkoxy, alkylthio or phenyl radicals.

A variety of compounds exhibiting leukotriene $B_4$ antagonist activity have been reported. These include compounds having chemical structures mimicking leukotriene structures such as Sumitomo's SM 9064, UpJohn's U-75360 and U-75302 and Ciba Geigy's CGS 23113. Other compounds, some of which include monocyclic ring structures and are disclosed in EP 276064, EP 276065 and EP 292977, are reported to exhibit both $LTD_4$ and $LTB_4$ antagonist properties.

The following publications disclose compounds related to those of the present invention but are neither disclosed herein nor are they disclosed for use for the purposes disclosed herein.

EP Publication No. 0090353 discloses pyridon-2 derivatives which have a 2–3 atom side chain having an ester group thereon and substitution of a 2- or 3-thienyl ring at the 6-position. These compounds are antiphlogistic agents.

EP Publication No. 0210084 discloses that bicyclic aryl and N-heteroaryl di- substituted amides are useful as anxiolytic agents.

JP Kokai Tokkyo Koho JP 82 58,666 discloses that pydidine and pyrimidine compounds having a thioalkyl side carboxy chain are anti-ulcer agents.

PCT International Publication No. WO89/11279 discloses nucleic acid interacting unfused heteropolycyclic compounds which inhibit translation and interfering with viral replication processes such as the replication of HIV.

The present invention is directed to a class of novel substituted bis-aryl and/or heteroaryl mono and/or bicyclic ring containing compounds which exhibit selective $LTB_4$ antagonist activity.

SUMMARY OF THE INVENTION

This invention relates to compounds having selective $LTB_4$ antagonist properties and comprising an aryl or heteroaryl mono- or bicyclic ring which has at least two substituents attached thereto; (1) a substituted or unsubstituted aryl or heteroaryl mono- or bicyclic ring and (2) a substituent chain having a terminal carboxylic acid functional group or derivative thereof attached thereto. This invention further relates to processes for their preparation and therapeutic compositions comprising said compound and methods for the treatment of disorders involving $LTB_4$ agonist-mediated activity utilizing said compositions.

More specifically the compounds of this invention are described by Formula I:

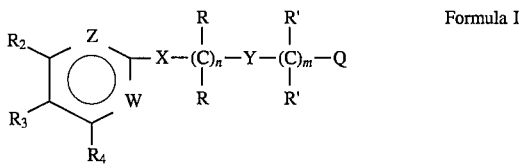

where
m is 1–8, n is 0–8 and n+m is 2–8;
X is S, O, NR", CR'R', CR'=CR', CO—NR", NR"—CO or a bond;
Y is S, O, NR", CR'R', CR'=CR', CO—NR", NR"—CO, CO, CR'—OH, phenylene, naphthylene or a nitrogen-containing cyclene group of the formula

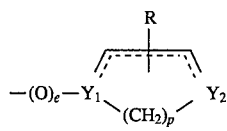

where $Y_1$ and $Y_2$ are independently CR' or N, p is 1–3. e is 0 or 1 and e is 0 when $Y_1$ is N;
W and Z are independently CR' or N provided that when both W and Z are N then n+m is 2–7;
R and R' are independently $R_1$ or $R_1$-loweralkyl- or vicinal R and/or R' groups together or vicinal R' and R" groups together may be —$(CH_2)_y$— where y is 2–4, thus forming a 4–6 membered ring and geminal R and/or R' groups may together form a spiro substituent, —$CH_2$—$(CH_2)_z$—$CH_2$— where z is 0–4 or an alkylidenyl substituent, =$CHR_5$, where $R_5$ is hydrogen or alkyl;
R" also may be hydrogen, alkyl or aralkyl;
$R_1$ is hydrogen, alkyl, alkenyl, cycloalkyl, aralkyl, aryl, hydroxy, alkoxy, aryloxy, aralkoxy, acyl, halo, amino, mono- and dialkylamino, aralkylamino, acylamino, carboxy, carbalkoxy, carbamyl or mono- and dialkylcarbamyl;
$R_2$, $R_3$ and $R_4$ are independently $R_1$, $R_1$-loweralkyl- or an optionally substituted mono- or bicyclic aryl or heteroaryl group containing about 5 to about 12 atoms wherein each ring comprising said group contains 0–2 hetero atoms selected from N, O or S provided said hetero atoms are not vicinal oxygen and/or sulfur atoms, and provided further that at least one of $R_2$, $R_3$ and $R_4$ is said aryl or heteroaryl group;
$R_2$, and $R_3$ or $R_3$ and $R_4$ together with the ring to which they are attached may form an optionally substituted fused bicyclic [5,6], [6,6] or [7,6] ring system which may contain from 0–2 hetero atoms in each ring selected from N, O and S, provided said hetero atoms are not vicinal oxygen and/or sulfur atoms;
$R_4$ also may be $X_1$—$(CH_2)_t$—$R_3$ provided that $R_3$ is said mono- or bicyclic aryl ring system, $X_1$ is S, O, NR", CR'R' or CO and t is 1–4; and Q is $COOR_6$, COOM, $CONR_7R_7$, CN, $CONHSO_2R_6$, tetrazolyl or tetrazolyl substituted with alkyl, carboxyalkyl or carbalkoxyalkyl, and

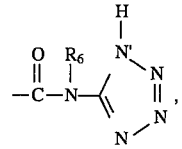

where $R_6$ is hydrogen, alkyl or aralkyl. $R_7$ is hydrogen, alkyl, aralkyl or cycloalkyl, M is a metal or ammonia salt and $R_7$ and $R_7$ together form a 3–6 membered ring provided that $R_7$ is hydrogen when $R_2$ and $R_3$ together and $R_3$ and $R_4$ together form a fused ring;
and pharmaceutically acceptable salts thereof.

DETAILED DESCRIPTION AND PREFERRED EMBODIMENTS

As employed above and throughout this disclosure, the following terms, unless otherwise indicated, shall be understood to have the following meanings:

"Bicyclic aryl" means a bicyclic ring system composed of two fused rings which may be partially or completely unsaturated carbocyclic and/or heterocyclic rings. More specifically, the bicyclic 6,6; 6,5; and 6,7 aryl ring systems are preferred and include naphthalene, quinazolines, benzazepines, quinoline, isoquinoline, and purine.

"Monocyclic aryl" means a partially or completely unsaturated carbocyclic or heterocyclic ring. Preferred monocycles include benzene, thiophene, pyridine, furan and pyrimidine.

"Aryl" refers to a partially or completely unsaturated carbocyclic or heterocyclic aromatic ring.

"Alkyl", either alone or with various substituents defined herein, means a saturated aliphatic hydrocarbon, either branched- or straight-chained. A "loweralkyl" is preferred having about I to about 6 carbon atoms. Examples of alkyl include methyl, ethyl, n-propyl, isopropyl, butyl, sec-butyl, t-butyl, amyl and hexyl.

"Alkoxy" refers to a loweralkyl-O-group.

"Alkenyl" refers to a hydrocarbon having at least one point of unsaturation and may be branched- or straight-chained. Preferred alkenyl groups have 2 to about 6 carbon atoms present. Exemplary alkenyl groups include vinyl, allyl, ethynyl and isopropenyl.

The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

"Halo" means a halogen. Preferred halogens Include chloride, bromide and fluoride. The preferred haloalkyl group is trifluoromethyl.

Still more specifically, this Invention may be described according to Formula I above by the following preferred embodiments (A)–(H):
(A) where m is 1 and n is 1–7;
X is S or O;
Y is O or $CH_2$;
Z is N and W is CR';
R and R' are independently hydrogen or alkyl;

$R_2$ and $R_4$ are independently hydrogen or an aryl group selected from phenyl, thienyl or furyl which may be substituted with 1-2 substituents independently selected from alkyl, alkoxy, methylenedioxy, halo, haloalkyl, alkylthio, nitro, amino, mono- and dialkylamino, acetamido, trifluoroacetamido or benzamido provided at least one of $R_2$ and $R_4$ is said aryl group;

$R_3$ is hydrogen or together with $R_2$ may form a fused benzene ring which may further be substituted with halo, alkyl or alkoxy; and Q is $COOR_6$, COONa, $CONR_7R_7$, or tetrazolyl where $R_6$ is hydrogen or alkyl and $R_7$ is hydrogen.

(B) where m is 2-7 and n is 0;

X is a bond;

Y is S or O;

W and Z are N;

R is hydrogen;

R' is independently hydrogen or $(CH_2)_x$—$R_1$, where x is 0-2 and where $R_1$ is hydrogen, alkyl, aralkyl, aryl or halo;

$R_2$, $R_3$ and $R_4$ are independently hydrogen or an aryl group selected from phenyl, thienyl or furyl which may be substituted with 1-2 substituents independently selected from alkyl, alkoxy, hydroxy, acetoxy, benzoyloxy, methylenedioxy, ethylenedioxy, aminomethyleneoxy, aminovinylene, halo, haloalkyl, alkylthio, nitro, amino, mono- and dialkylamino, acetamido, ureido, trifluoroacetamido or benzamido or an aryl group selected from imidazole, thiazole or pyridyl which may be substituted with 1-2 substituents independently selected from alkyl, alkoxy, hydroxy, acetoxy, benzoyloxy, halo, haloalkyl, alkylthio, nitro, amino, mono- and dialkylamino, acetamido, trifluoroacetamido or benzamido provided at least one of $R_2$, $R_3$ and $R_4$ is said aryl group;

$R_3$ is hydrogen or alkyl or together with $R_2$ may form a fused benzene ring which may further be substituted with halo, alkyl or alkoxy; and Q is $COOR_6$, COONa, $CONR_7R_7$ or tetrazolyl where $R_6$ is hydrogen or alkyl and $R_7$ is hydrogen.

(C) where m is 2-7 and n is 0

X is a bond;

Y is S or O;

Z is N and W is CR';

R is hydrogen;

R' is independently hydrogen or $(CH_2)_x$—$R_1$, where x is 0-2 and where $R_1$ is hydrogen, alkyl, aralkyl, aryl or halo;

$R_2$, $R_3$ and $R_4$ are independently hydrogen, alkyl or an aryl group selected from phenyl, thienyl or furyl which may be substituted with 1-2 substituents independently selected from alkyl, alkoxy, hydroxy, acetoxy, benzoyloxy, methylenedioxy, ethylenedioxy, aminoethylene, aminomethyleneoxy, aminovinylene, halo, haloalkyl, alkylthio, nitro, amino, mono- and dialkylamino, acetamido, ureido, trifluoroacetamido or benzamido or an aryl group selected from imidazol, thiazol or pyridyl which may be substituted with 1-2 substituents independently selected from alkyl, alkoxy, hydroxy, acetoxy, benzoyloxy, halo, haloalkyl, alkylthio, nitro, amino, mono- and dialkylamino, acetamido, trifluoroacetamido or benzamido provided at least one of $R_2$, $R_3$ and $R_4$ is said aryl group and more than one said aryl groups are ortho to each other; and Q is $COOR_6$, COONa, $CONR_7R_7$, or tetrazolyl where $R_6$ and $R_7$ are independently hydrogen or alkyl.

(D) where m is 2-7 and n is 0;

X is S or O;

Y is a bond;

Z is N and W is CR';

R is hydrogen;

R' is independently hydrogen or $(CH_2)_x$—$R_1$, where x Is 0-2 and $R_1$ is hydrogen, alkyl, aralkyl, aryl or halo;

$R_2$, $R_3$ and $R_4$ are independently hydrogen, R' or an aryl group selected from phenyl, thienyl or furyl which may be substituted with 1-2 substituents Independently selected from alkyl, alkoxy, methylenedioxy, halo, haloalkyl, alkylthio, nitro, amino, mono- and dialkylamino, acetamido, trifluoroacetamido or benzamido provided at least one of $R_2$, $R_3$ and $R_4$ is said aryl group; and Q is $COOR_6$, COONa, $CONR_7R_7$, or tetrazolyl where $R_6$ and $R_7$ are ; independently hydrogen or alkyl.

(E) where n is 0-4, m is 1-5 and n+m 2-6;

X is S, O, CR'=CR' or CHR'—O;

Y is phenyl or a heterocyclic ring of the formula where $Y_1$ and $Y_2$ are independently CR' or N and p is 1-3;

Z is N and W is CR';

R and R' are independently hydrogen or $(CH_2)_x$—$R_1$, where x is 0-2;

$R_1$ is hydrogen, alkyl, aralkyl, aryl or halo;

$R_2$ is hydrogen, cycloalkyl or an aryl group selected from phenyl, thienyl or furyl which may be substituted with 1-2 substituents independently selected from alkyl, alkoxy, methylenedioxy, halo, haloalkyl, alkylthio, nitro, amino, mono- and dialkylamino, acetamido, trifluoroacetamido or benzamido;

$R_3$ is hydrogen;

$R_4$ is hydrogen or an aryl group selected from phenyl, thienyl or furyl which may be substituted with 1-2 substituents independently selected from alkyl, alkoxy, methylenedioxy, halo, haloalkyl, alkylthio, nitro, amino, mono- and dialkylamino, acetamido, trifluoroacetamido or benzamido; provided at least one of $R_2$ and $R_4$ is said aryl group; and Q is $COOR_6$, COONa, $CONR_7R_7$, or tetrazolyl where $R_6$ and $R_7$ are independently hydrogen or alkyl.

(F) where m is 1-4 and n is 1-5;

X is S or O;

Y is CO—NR", NR"—CO, CO or CR'OH;

Z is N and W is CR';

R is hydrogen;

R' is independently hydrogen, or $(CH_2)_x$—$R_1$, where x is 0-2;

R" is hydrogen, alkyl or aralkyl;

$R_1$ is hydrogen, alkyl, aralkyl, aryl or halo;

$R_2$ is hydrogen, alkyl,cycloalkyl or an aryl group selected from phenyl, thienyl or furyl which may be substituted with 1-2 substituents Independently selected from alkyl, alkoxy, methylenedioxy, halo, haloalkyl, alkylthio, nitro, amino, mono- and dialkylamino, acetamido, trifluoroacetamido or benzamido;

$R_3$ is hydrogen;

$R_4$ is hydrogen or an aryl group selected from phenyl, thienyl or furyl which may be substituted with 1-2 substituents independently selected from: alkyl, alkoxy, methylenedioxy, halo, haloalkyl, alkylthio, nitro, amino, mono- and dialkylamino, acetamido, trifluoroacetamido or benzamido provided at least one of $R_2$ and $R_4$ is said aryl group; and Q is $COOR_6$, COONa, $CONR_7R_7$, or tetrazolyl where $R_6$ and $R_7$ are independently hydrogen or alkyl.

(G) where m+n=2-7;

X is S, O, CR'R' or CR'=CR';

Y is CR'R';

Z and W are CR';

R is independently hydrogen or alkyl;

R' is independently hydrogen, alkyl, aralkyl, aryl or halo;

$R_2$, is hydrogen, alkyl, cycloalkyl or an aryl group selected from phenyl, thienyl or furyl which may be substituted with 1-2 substituents independently selected from alkyl, alkoxy, methylenedioxy, halo, haloalkyl, alkylthio, nitro, amino, mono- and dialkylamino, acetamido, trifluoroacetamido or benzamido;

$R_3$ is hydrogen or alkyl;

$R_2$ and $R_3$ together may form a fused benzene ring which may be substituted with a substituted or unsubstituted $R_1$ mono- or bicyclic aryl ring and/or further substituted with halo, alkyl, alkoxy or aralkoxy;

$R_4$ is hydrogen or an aryl group selected from phenyl, thienyl or furyl which may be substituted with 1–2 substituents independently Selected from alkyl, alkoxy, methylenedioxy, halo, haloalkyl, alkylthio, nitro, amino, mono- and dialkylamino, acetamido, trifluoroacetamido or benzamido provided at least one of $R_2$ and $R_4$ is said aryl group; and It is essential that the aryl ring described by Formula I has attached thereon at least one of the second aryl function groups. This may be attached as in Formula I as at least one of $R_2$, $R_3$ and $R_4$ or when $R_2$ and $R_3$ together or $R_3$ and $R_4$ together are a fused ring it may be attached to the formed fused ring. This second aryl function may be optionally substituted by alkyl, alkoxy, hydroxy, methylenedioxy, halo, haloalkyl, thio, alkylthio, nitro, amino, mono- and dialkylamino, cycloalkylamino, acetamido, trifluoroacetamido, benzamido, carboxy, carbalkoxy, carbaralkoxy, carbamyl, mono- and dialkylcarbamyl or arylcarbamyl.

The preferred position for the attachment of the second aryl function is meta to the chain having a terminal carboxylic acid functional group or derivative.

Among the most preferred chains having a terminal carboxylic acid functional group are:

—$(CH_2)_{m+n}$—CR'R'—Q where m+n is 3–7,

—$(CH_2)_n$—CH=CH—$(CH_2)_m$—CR'R'—Q where m+n is 1–5,

—O—$(CH_2)_{m+n}$—CR'R'—Q where m+n is 3–7,

—O—$(CH_2)_n$—CH=CH—$(CH_2)_m$—CR'R'—Q where m+n is 1–5; and where R' is hydrogen or lower alkyl and Q is tetrazolyl, —$COOR_6$ where $R_6$ is hydrogen or alkyl, COOM or $CONR_7R_7$ where M is an alkali metal, $R_7$ is hydrogen or alkyl, or $R_7$ and $R_7$ together with the nitrogen to which they are attached form a 5–6 membered nitrogen-containing ring.

In addition to the two substituents attached to the aryl or heteroaryl mono- or bicyclic ring system as described above, it is often desirable to have a third substituent present. This may be the same or different as these already present in the molecule. It is preferred that such third substituent also be one described above as a second aryl substituent. This may be the same or different as that already present and it is further preferred that such substituent also be in the meta position to the acid chain function. In those formulae where Z and/or W are nitrogen, it is preferred that both $R_2$ and $R_4$ are a second aryl function.

Q is $COOR_6$, COONa, $CONR_7R_7$, or tetrazolyl where $R_6$ is hydrogen or alkyl and $R_7$ is hydrogen.

(H) where m+n=2–7;

X is S, O, CR'R' or CR'=CR';

Y is CR'R';

Z is N or CR' and W is CR';

R is hydrogen;

R' is Independently hydrogen, alkyl, aralkyl, aryl or halo;

R" is hydrogen or alkyl;

$R_2$ hydrogen, alkyl, cycloalkyl halo or an aryl group selected from : phenyl, thienyl or furyl which may be substituted with 1–2 substituents independently selected from alkyl, alkoxy, methylenedioxy, halo, haloalkyl, alkylthio, nitro, amino, mono- and dialkylamino, acetamido, trifluoroacetamido or benzamido;

$R_3$ hydrogen or an aryl group selected from phenyl, thienyl or furyl which may be substituted with 1–2 substituents independently selected from alkyl, alkoxy, methylenedioxy, halo, haloalkyl, alkylthio, nitro, amino, mono- and dialkylamino, acetamido, trifluoroacetamido or benzamido provided at least one of $R_2$ and $R_4$ is said aryl group;

$R_4$ is $X_1$—$(CH_2)_q$—$R_3$ where $X_1$ is O, NR", CR'R' or CO and q is 1–4;and Q is $COOR_6$, COONa, $CONR_7R_7$, or tetrazolyl where $R_6$ and $R_7$ are independently hydrogen or alkyl.

Turning now to the two substituents which are attached to the aryl or heteroaryl mono- or bicyclic ring system described by Formula I. The preferred first substituent is a substituted or unsubstituted aryl or heteroaryl mono- or bicyclic ring and which will be referred to in this case as the second aryl function. The preferred second substituent is a chain having a terminal carboxylic acid functional group or derivative thereof which is described by

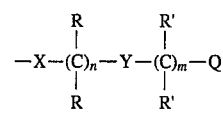

where X, Y, Q, R, R', n and m are as described above.

The compounds of this invention may be prepared by employing art recognized procedures from known compounds or readily preparable intermediates. Exemplary general procedures are as follows:

Since the compounds of this invention have at least two substituents which are present, the introduction of each substituent to the aryl ring system is, of course, dependent on the specific substituents involved and the Chemistry necessary for their formation. Thus, consideration of how one substituent would be affected by a chemical reaction when forming a second substituent would involve techniques familiar to the skilled artisan. This would further be dependent on the bicyclic ring system involved.

It is convenient to synthesize these molecules by employing condensation reactions at reactive X and Y sites of the molecule. Exemplary general procedures are as follows and are basic to developing the molecules having the required substituents present. The substitution patterns for each of the mono- and bicyclic rings would depend on the chemistry of the particular ring. Any such adjustments to the chemistry would be familiar to one skilled in the art.

Thus, in order to prepare those compounds where X or Y is O, S or NR' the following reactions or combination of reactions may be employed:

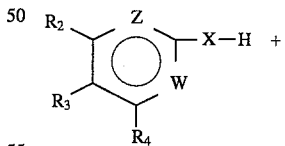

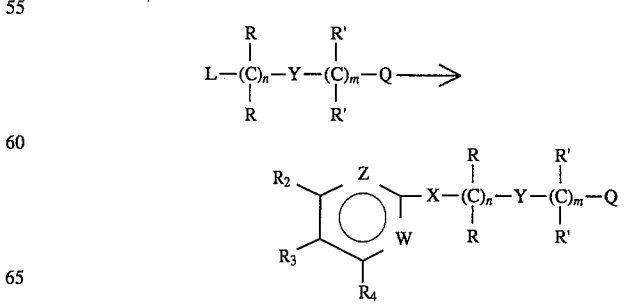

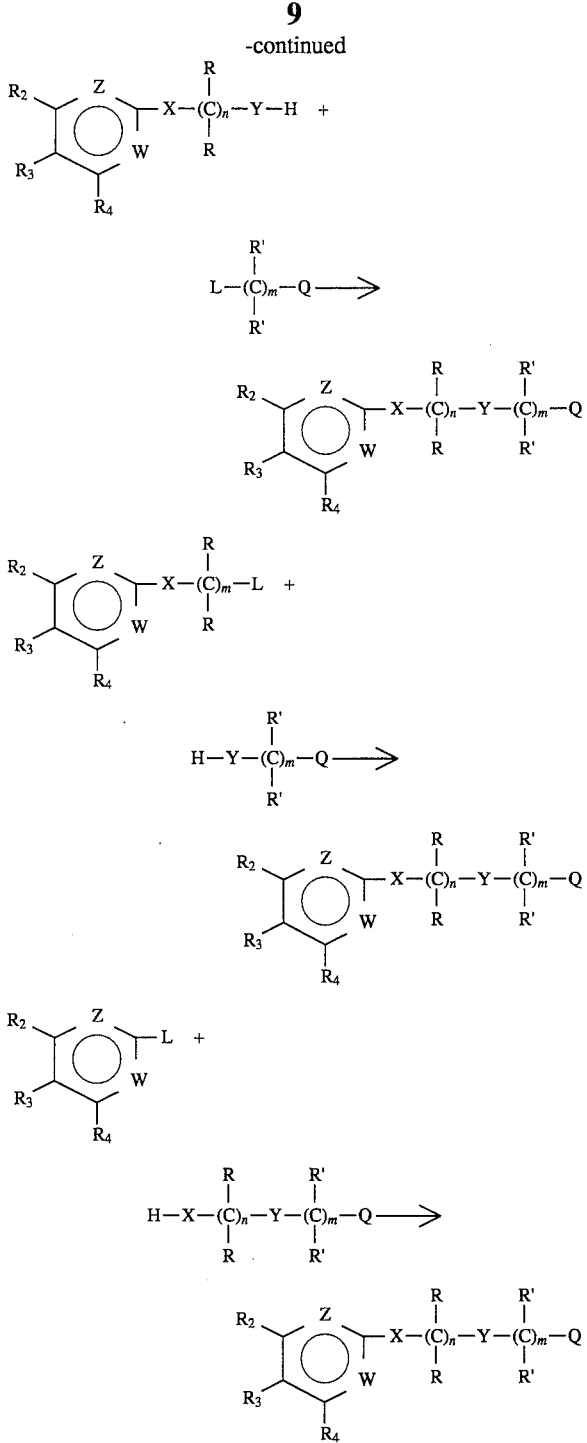

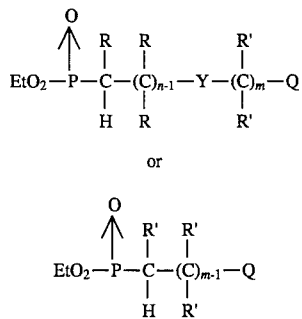

When X or Y is O or S, the compounds may be prepared by condensation of an aryl or heteroaryl alcohol or thiol with a compound of the formulae L—(CRR)$_n$—(CR'R')$_m$—Q or L—(CR'R')$_m$—Q where Q is preferably a nitrile, ester or tetrazole and L is a leaving group such as halo (preferably bromo), tosylate or mesylate.

The reaction is generally carded out in the presence of any basic medium normally employed to deprotonate an alcohol or thiol, in particular an alkaline alcoholate, an alkaline hydride, or a carbonate (for example potassium tertbutylate, sodium ethylate, sodium hydride, sodium hydroxide, triethylamine, silver carbonate, potassium carbonate, sodium carbonate, diisopropyl/ethylamine or methyl magnesium halides.), in an organic solvent such as an alcohol (for example ethanol, i-propanol, etc.), an aromatic hydrocarbon (for example toluene), an amide (for example dimethylformamide) or an oxide (for example dimethyl sulphoxide), at a temperature of between 30 minutes to 96 hours depending on the substituents present. The reaction is usually carded out in a solvent that will dissolve both reactants and is inert to both as well. Solvents include, but are not limited to diethyl ether, THF, N,N-dimethylformamide, dimethyl-sulfoxide, dioxane and the like.

It is understood that when $R_1$, $R_2$, $R_3$ and $R_4$ carry an amino or alkylamino radical, or when a product of general formula I for which Q is a 5tetrazolyl radical is allowed to react, it is necessary to protect the amino radicals by any method which does not modify the rest of the molecule. The protection is carded out by any known method for the protection of amines and in which the introduction of the radical and its removal does not affect the rest of the molecule. In particular, there are used the methods described by T. W. Greene, Protective Groups in Organic Synthesis, A. Wiley—Interscience Publication (1981), or by Mc Omie, Protective Groups in Organic Chemistry. By way of example, the protective radicals may be chosen from among methoxycarbonyl, ethoxycarbonyl, t-butoxycarbonyl, allyloxycarbonyl, vinyloxycarbonyl, benzyloxycarbonyl or its substituted derivatives, trichloroethoxycarbonyl, formyl, acetyl, trichloroacetyl, trifluoroacetyl, chloroacetyl, trityl, benzhydryl, benzyl or allyl.

When X is an alkyl group, it is convenient to prepare these compounds by Friedel-Crafts alkylation or by the Wittig reaction followed by reduction.

Those compounds where X and/or Y are CR'═CR' are prepared by reacting the appropriate aldehyde or ketone with an appropriate Wittig reagent or modified Wittig reagent of the formula where Q is cyano or carbalkoxy.

Reference for the Wittig reaction and modified Wittig reaction to control the formation of the trans and cis configuration at the double bond and the isomerization of cis and trans isomers can be found in A. Maercher, *Organic Reactions*, 14, 270,1965.

The intermediate aldehyde compounds may be prepared in the usual manner from the corresponding carboxylic acid with an alkyllithium reagent, or from the oxidation of the corresponding alcohol. The aldehyde can also be obtained by Friedel-Crafts acylation or formylation (POCl$_3$ /DMF).

When X and/or Y are NR"—CO or CO—NR" then the condensation of an acid or an acid halide with the appropriate aryl amine will give the desired compound.

When it is desired to prepare a product for which Q is a carboxy radical, condensation is carded out on the ester and then converted to an acid. Hydrolysis of the ester is carded out according to the usual methods, in particular in basic medium by the action of an alkaline base such as sodium hydroxide or potassium hydroxide, in alcoholic or hydroalcoholic solution (for example in ethanol-water or methanol-water medium), at a temperature of between 20° C. and the reflux temperature of the reaction mixture. It is also possible to carry out the reaction in the presence of a lithium halide in collidine, preferably under inert atmosphere, at the reflux temperature of the reaction mixture.

When it is desired to obtain a product for which Q is an alkoxy-carbonyl radical, the acid obtained is convened to an ester. The reaction is carded out in a basic medium, for example in the presence of a base such as an alkaline alcoholate, an alkaline hydride or a carbonate in an organic solvent such as an alcohol (for example ethanol, i.propanol), an amide (for example dimethylformamide), an aromatic hydrocarbon (for example toluene), or an oxide (dimethyl sulphoxide), at a temperature of between 50° and 120° C.

Conversion of the nitrile to an acid is carried out by acid or basic hydrolysis, for example by sulphuric acid in aqueous medium, at the reflux temperature of the reaction mixture or by potassium hydroxide in aqueous or hydroalcoholic medium, at the reflux temperature of the reaction mixture.

Conversion of the nitrile to a 5-tetrazolyl radical Is carded out by treating an alkaline nitride for example sodium nitride. The reaction is carried out in the presence of ammonium chloride in an organic solvent such as an amide (for example dimethylformamide, dimethylacetamide), at a temperature of between 80° and 150° C.:

Conversion of the nitrile into an amide is carried out by hydration in acid medium, for example by treating in formic acid/hydrochloric acid medium, at a temperature of about 20° C.

The tetrazoles may be formed from the nitrile at various stages of the synthesis by treating an alkaline nitride for example sodium nitride. The reaction is carried out in the presence of ammonium chloride in an organic solvent such as an amide (for example dimethylformamide, dimethylacetamide), at a temperature of between 80° and 150° C. The tetrazoles may also be formed with hydrazoic acid formed in situ from sodium azide and an acid.

Various substituents on the present new compounds, e.g., as defined in $R_1$ and substitution on the aryl or heteroaryl rings of $R_1$, $R_2$ or $R_3$ or where $R_2$ and $R_3$ together or $R_3$ and $R_4$ together, can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then by transformed to the corresponding alkyl groups by various methods, Including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

More specifically, when it is desired to obtain a product which contains an amino substituent this may be obtained from the corresponding nitro derivative by any known method for reducing a nitro radical without affecting the rest of the molecule. The reaction is advantageously carried out by reducing with stannous chloride, in an organic solvent such as an alcohol, for example ethanol, at the reflux temperature of the reaction mixture.

According to the invention, the products of general formula I which contain a mono- or dialkylamino, benzoylamino or trifluoroacetamido substituent may also be obtained from the corresponding derivative which bears an amino substituent, by any known method for alkylating or acylating an amine without affecting the rest of the molecule. The alkylating reaction may be implemented by the action of ethyl orthoformate or the corresponding carbonyl derivative, in acid or neutral medium, followed by reduction for example by sodium borohydride. The acylating reaction is carried out in particular by the action of a reactive derivative of the acid, for example the acid chloride, the anhydride, a mixed anhydride or a reactive ester, in an organic solvent such as a chlorinated solvent (for example dichloromethane, dichloroethane, chloroform), an amide (for example dimethylacetamide, dimethylformamide), in the presence of an acid acceptor such as an azotized organic base (for example triethylamine, dimethylaminopyridine, N-methylmorpholine), at a temperature of between −40° and +40° C. The reaction is carded out in an organic solvent such as for example toluene at the reflux temperature of the reaction mixture.

The starting materials for this invention are either known or can be prepared by known processes in the art. For example, the thioalcohols may be prepared by the action of phosphorus pentasulphide on the corresponding hydroxyl derivative followed by the condensation reaction as above.

The heterocyclic alcohol starting materials may be prepared by the action of an ∝-ethylenic ketone of general formula $R_2CO—CH=CHR_4$ wherein $R_1$ and $R_4$ are as previously defined, on an N-carbamoylmethylpyridinium salt [prepared according to the method described by O. ALBRECHT et al., Helv. Chim. Acta 24, 241E (1941)], in the presence of a base such as for example sodium hydroxide, followed by treatment in acid medium, at a temperature of about 20° C.

The heterocyclic alcohol starting materials where $R_2$ forms with $R_3$ a benzene ring, optionally substituted, may be prepared from a substituted ketoamide of general formula $R_4—CO—CH_2—CONH—Ph$, wherein $R_4$ is as previously defined and substitution therein may be halogen, alkyl or alkoxy radical, by treating in acid medium. The reaction may be carried out in sulphuric acid, preferably aqueous sulfuric acid, at a temperature of about 100° C.

Other starting materials which are nitriles or alcohols may be prepared by analogous methods described for the preparation of products according to the invention.

The products according to the invention may be purified by known physical methods such as crystallization, distillation or chromatography.

Certain compounds of this invention may have at least one asymmetric carbon atom such as those compounds having different geminal R or R' groups. Further, certain compounds of this invention may exist in their cis or trans configuration such as those compounds where X and/or Y is CR'=CR'. As a result, those compounds of this invention may be obtained either as racemic mixtures, diastereoisomeric mixtures or as individual enantiomers. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al, J. Am. Chem. Soc. 96, 3642, 1974.

It is to be understood that the scope of this invention encompasses not only the various isomers which may exist but also the various mixture of isomers which may be formed. The resolution of the compounds of this invention and their starting materials may be carded out by known procedures. Incorporation by reference is hereby made to the four volume compendium *Optical Resolution Procedures for Chemical Compounds:* Optical Resolution Information Center, Manhattan College, Riverdale, N.Y. Such procedures are useful in the practive of this invention. A further useful reference is *Enantiomers, Racemates and Resolutions:* Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases.

When Q represents a carboxy radical, the products according to the present invention may be converted to metal salts or to addition salts with an azotized base, according to methods known per se. These salts may be obtained by the action of a metallic base (for example an alkali metal or alkaline-earth metal base), of ammonia or of an amine, on a product according to the invention, in a suitable solvent, or by exchange reaction with an organic acid salt. The salt formed precipitates after optional concentration of the solution, it is separated by filtration, decantation or freeze-drying. By way of examples of pharmaceutically acceptable salts, there may be mentioned salts of alkali metals (sodium, potassium, lithium) or of alkaline-earth metals (magnesium, calcium), ammonium salts and azotized base salts (ethanolamine, diethanolamine, triethylamine, trimethylamine, methylamine, propylamine, diisopropylamine, NN-dimethylethanolamine, benzylamine, dicyclohexylamine, N-benzyl-13-phenethylamine, NN'-dibenzylethylenediamine, diphenylenediamine, benzhydrylamine, quinine, choline, arginine, lysine, leucine, dibenzylamine). When the product of general formula I bears amino or alkylamino radicals, the latter may be convened to addition salts with the acids. By way of examples of addition salts of the pharmaceutically acceptable acids, there may be mentioned salts formed with inorganic acids (hydrochlorides, hydrobromides, nitrates, sulphates, phosphates) or with organic acids (succinates, fumarates, tartrates, acetates, propionates, maleates, citrates, methanesulphonates, paratoluenesulphonates, isothionates or with substitution derivatives of these compounds).

When Q represents a 5-tetrazolyl radical, the products according to the present invention may be convened to metal salts with strong bases. These salts may be obtained by the action of a strong metal base on a product according to the invention in a suitable solvent. By way of examples of pharmaceutically acceptable salts, there may be mentioned the salts of alkali metals (sodium, potassium, lithium).

The following examples are given without implying any limitation and are representative to illustrate the present invention.

In the following examples, chromatographies under pressure are carded out under a pressure of about 50 kPa; solvent evaporations are carded out under a pressure of about 3.3 kPa.

EXAMPLE 1

4,6-diphenyl,2-pyridone

To a solution of benzylideneacetophenone (41.6 g) and N-carbamoylmethylpyridinium chloride (34.4 g) (prepared according to the method of O. ALBRECHT et al., Helv. Chim. Acta 24, 241E (1941)) in methanol (600 cc), is added, at room temperature, a 1N aqueous solution of sodium hydroxide (200 cc). The initially yellow solution takes on an orange colour and a yellow solid precipitates. The mixture is stirred at room temperature for 15 minutes and acetic acid (400 cc) Is then added. The green solution obtained is stirred for 1 hour at room temperature. The solvent Is then distilled in 4 hours under atmospheric pressure. The solid residue obtained is taken up in distilled water (500 cc). After stirring for 1 hour at room temperature, the solid is separated by filtration, washed with distilled water (3×100 cc) and dried under reduced pressure at 60° C. (whitish solid; m.p.= 209°–212° C.).

EXAMPLE 2

4-(4-chlorophenyl)-6-phenyl-2-pyridone

The procedure in Example 1 is followed but using 3-(4-chlorophenyl)- 1-phenyl-2-propen-1-one (10 g), N-carbamoylmethylpyridinium chloride (7.1 g), methanol (150 cc), a 1N aqueous solution of sodium hydroxide (40 cc) and acetic acid (80 cc). The product is purified by chromatography under pressure on silica gel (30–60 mm; eluent: methylene chloride-methanol: 95-5). (yellowish solid; m.p.=241°–243° C.)

When the procedure of Example 2 is followed and 3-(4-chlorophenyl)- 1-phenyl-2-propen-1-one is replaced by the compounds of Table I below then the corresponding products of Table II below are prepared.

Table I 3-(4-methoxyphenyl)-1-phenyl-2-propen-1-one
1-(4-methoxyphenyl)-3-phenyl-2-propen-1-one
1-(4-trifluoromethylphenyl)-3-phenyl-2-propen-1-one
1,3-di(4-chlorophenyl)-2-propen-1-one
1-(4-methylphenyl)-3-phenyl-2-propen-1-one
1-(4-chlorophenyl)-3-(4-methoxyphenyl)-2-propen-1-one
3-(4-chlorophenyl)-1-(4-methoxyphenyl)-2-propen-1-one
3-(2-fluorophenyl)-1-phenyl-2-propen-1-one
1-phenyl-3-(4-trifluoromethylphenyl)-2-propen-1-one
3-(3-methoxyphenyl)-1-phenyl-2-propen-1-one
1,3-di(4-methoxyphenyl)-2-propen-1-one
3-(4-fluorophenyl)-1-phenyl-2-propen-1-one
1-(4-fluorophenyl)-3-phenyl-2-propen-1-one
1-(2-fluorophenyl)-3-phenyl-2-propen-1-one
1-(3-methoxyphenyl)-3-phenyl-2-propen-1-one
3-(3,4-dichlorophenyl)-1-phenyl-2-propen-1-one 3-(4-methylphenyl)-1-phenyl-2-propen-1-one
3-(3-chlorophenyl)-1-phenyl-2-propen-1-one
1-(2-chlorophenyl)-3-phenyl-2-propen-1-one
3-(2-chlorophenyl)-1-phenyl-2-propen-1-one
1-(3-fluorophenyl)-3-phenyl-2-propen-1-one
4-(3-Fluorophenyl)-6-phenyl-2-pyridone
3-(4-fluorophenyl)-1-(2-fluorophenyl)-2-propen-1-one
3-(4-methylthiophenyl)-1-phenyl-2-propen-1-one
3-(3,4-methylenedioxyphenyl)-1-phenyl-2-propen-1-one
3-(3-methylphenyl)-1-phenyl-2-propen-1-one
3-(4-dimethylaminophenyl)-1-phenyl-2-propen-1-one
3-(4-nitrophenyl)-1-phenyl-2-propen-1-one
3-(3-nitrophenyl)-1-phenyl-2-propen-1-one
3-phenyl-1-(2-thienyl)-2-propen-1-one
3-phenyl-1-(3-thienyl)-2-propen-1-one
1-(2-chlorophenyl)-3-(3,4-methylenedioxyphenyl)-2-propen-1-one
3-(4-chlorophenyl)-propenal
2,2-dimethyl-5-phenyl-4-penten-3-one
4-phenyl-3-buten-2-one
1-cyclo-propyl-3-phenyl-2-propen-1-one
1-phenyl-3-(3,4-dimethoxyphenyl)-2-propen-1-one
1-phenyl-3-(4-cyanophenyl)-2-propen-1-one
1-phenyl-3-(3,5-dimethoxyphenyl)-2-propen-1-one Table II 4-(4-methoxyphenyl)-6-phenyl-2-pyridone (yellowish solid; m.p.=227°–229° C.)
6-(4-methoxyphenyl)-4-phenyl-2-pyridone (whitish solid; m.p.=243°–245° C.)
6-(4-trifluoromethylphenyl)-4-phenyl-2-pyridone (whitish solid)
4,6-di(4-chlorophenyl)-2-pyridone white solid; (m.p.=297°–298° C.)
6-(4-methylphenyl)-4-phenyl-2-pyridone (whitish solid)
6-(4-chlorophenyl)-4-(4-methoxyphenyl)-2-pyridone (m.p.=264° C.)
4-(4-chlorophenyl)-6-(4-methoxyphenyl)-2-pyridone (m.p.=270° C.)
4-(2-fluorophenyl)-6-phenyl-2-pyridone (m.p.=211°–213° C.)
6-phenyl-4-(4-trifluoromethylphenyl)-2-pyridone (m.p.=228°–229° C.)
4-(3-methoxyphenyl)-6-phenyl-2-pyridone (m.p.=187°–188° C.)
4,6-di-(4-methoxyphenyl)-2-pyridone (m.p.=260°–262° C.)
4-(4-fluorophenyl)-6-phenyl-2-pyridone (m.p.=215° C.)
6-(4-fluorophenyl)-4-phenyl-2-pyridone (m.p.=220° C.)
6-(2-fluorophenyl)-4-phenyl-2-pyridone (m.p.=224°–225° C.)
6-(3-methoxyphenyl)-4-phenyl-2-pyridone (m.p.=202°–203° C.)
4-(3,4-dichlorophenyl)-6-phenyl-2-pyridone (m.p.=247° C.)
4-(4-methylphenyl)-6-phenyl-2-pyridone (m.p.=248° C.)
4-(3-chlorophenyl)-6-phenyl-2-pyridone (m.p.=209°–210° C.)
6-(2-chlorophenyl)-4-phenyl-2-pyridone (m.p.=213° C.)
4-(2-chlorophenyl)-6-phenyl-2-pyridone (m.p.=238° C.)
6-(3-fluorophenyl)-4-phenyl-2-pyridone (m.p.=248° C.)
4-(3-fluorophenyl)-6-phenyl-2-pyridone (m.p.=201° C.)
4-(4-fluorophenyl)-6-(2-fluorophenyl)-2-pyridone (m.p.=225°–226° C.)
4-(4-methylthiophenyl)-6-phenyl-2-pyridone (m.p.=228° C.)
4-(3,4-methylenedioxyphenyl)-6-phenyl-2-pyridone (m.p.=254°–255° C.)
4-(3-methylphenyl)-6-phenyl-2-pyridone (m.p.=211° C.)
4-(4-dimethylaminophenyl)-6-phenyl-2-pyridone (m.p.=254°–256° C.)
4-(4-nitrophenyl)-6-phenyl-2-pyridone (m.p.=284°–285° C.)
4-(3-nitrophenyl)-6-phenyl-2-pyridone (m.p.=210° C.)
4-phenyl-6-(2-thienyl)-2-pyridone (m.p.=212°–215° C.)
4-phenyl-6-(3-thienyl)-2-pyridone (m.p.=192°–195° C.)
6-(2-chlorophenyl)-4-(3,4-methylenedioxyphenyl)-2-pyridone (m.p.>260° C.)
4-(4-chlorophenyl)-2-pyridone (whitish solid)
6-ter-butyl-4-phenyl-2-pyridone (m.p.=215°–217° C.)
6-methyl-4-phenyl-2-pyridone (m.p.=199°–201° C.)
6-cyclo-propyl-4-phenyl-2-pyridone (m.p.=207°–209° C.)
6-phenyl-4-(3,4-dimethoxyphenyl)-2-pyridone (m.p.=233° C.)
6-phenyl-4-(4-cyanophenyl)-2-pyridone (m.p.=262° C.)
6-phenyl-4-(3,5-dimethoxyphenyl)-2-pyridone (m.p.=256° C.).

EXAMPLE 3

4-phenyl-2-quinolinone

Benzoylacetanilide (150 g) (prepared according to the method of Brown et al., J. Am. Chem. Sot., 79, 2919, (1957)) in concentrated sulphuric acid (76%) (130 cc) is heated for 4 hours at 100° C. The reaction mixture is slowly poured with stirring in distilled water (3150 cc). The precipitate obtained is filtered, washed with water and then with acetone, and dried at 40° C. under reduced pressure. The residue obtained is recrystallised in ethanol. (white solid; m.p.=268°–269° C.)

When the procedure of Example 3 is followed and benzoylacetanilide is replaced by the compounds of Table III below then the corresponding products of Table IV below are prepared.

Table III (4-chlorobenzoyl)acetanilide
(3-chlorobenzoyl)acetanilide
(2-fluorobenzoyl)acetanilide
(4-fluorobenzoyl)acetanilide
(3,4-dichlorobenzoyl)acetanilide
(4-chlorobenzoyl)acetanilide
(3-chlorobenzoyl)acetanilide
(4-nitrobenzoyl)acetanilide
(3-methoxybenzoyl)acetanilide
(4-methoxybenzoyl)acetanilide
(4-methylthiobenzoyl)acetanilide
(3-toluoyl)acetanilide
(4-toluoyl)acetanilide
(3-methylbenzoyl)acetanilide
(4-trifluoromethylbenzoyl)acetanilide
(4-dimethylaminobenzoyl)acetanilide
2-methyl-3-oxo-3-phenyl-propanilide
benzoyl-p-acetoluidide
(2-methoxybenzoyl)acetanilide
benzoyl-4'-methoxy-acetanilide
4-(4-chlorophenyl)-2-quinolinone (m.p.=247°–250° C.)
4-(3-chlorophenyl)-2-quinolinone (m.p.=233° C.)
4-(2-fluorophenyl)-2-quinolinone (m.p.=258° C.)
4-(4-fluorophenyl)-2-quinolinone (m.p.=253°–254° C.)
4-(3,4-dichlorophenyl)-2-quinolinone (m.p.=255° C.)
6-chloro-4-phenyl-2-quinolinone (m.p.=258° C.)
7-chloro-4-phenyl-2-quinolinone (m.p.=269° C.)
4-(4-nitrophenyl)-2-quinolinone (m.p.=302°–303° C.)

4-(3-methoxyphenyl)-2-quinolinone (white solid)
4-(4-methoxyphenyl)-2-quinolinone (white solid)
4-(4-methylthiophenyl)-2-quinolinone (m.p.=226° C.)
4-(3-tolyl)-2-quinolinone (m.p.=209°–210° C.)
4-(4-tolyl)-2-quinolinone (m.p.=238°–240° C.)
7-methyl-4-phenyl-2-quinolinone (m.p.=267° C.)
4-(4-trifluoromethylphenyl)-2-quinolinone (m.p.>350° C.)
4-(4-dimethylaminophenyl)-2-quinolinone (m.p.= 290°–293° C.)
4-phenyl-3-methyl-2-quinolinone (m.p.=240°–241° C.)
4-phenyl-6-methyl-2-quinolinone (m.p.=247° C.)
4-(2-methoxyphenyl)-2-quinolinone (m.p.=241° C.)
6-methoxy-4-phenyl-2-quinolinone (m.p.=253° C.).

EXAMPLE 4 ethyl 6-[(4,6-diphenyl-2-pyridyl)oxy]hexanoate

A suspension obtained by mixing 4,6-diphenyl-2-pyridone (2.5 g), ethyl 6-bromohexanoate (3.4 g) and silver carbonate (1.4 g) in toluene (100 cc) is refluxed, protected from light, for 24 hours. After filtration of the reaction mixture, the filtrate is concentrated to dryness at 40° C. under reduced pressure. The oily residue obtained is purified by chromatography under pressure, on silica gel (30–60 mm; eluent: n-hexane-ethyl acetate 92-8) (yellowish oil).

When the procedure of Example 4 is followed and 6-bromohexanoate is replaced by the compounds of Table V below, then the corresponding product is prepared.

Table V methyl 6-bromo-2,2-dimethylhexanoate
ethyl 7-bromoheptanoate
ethyl 4-bromobutanoate
ethyl 6-bromohexanoate
ethyl 6-bromohexanoate
ethyl 6-bromo-2-methylhexanoate
methyl 6-bromo-2,2-dimethylhexanoate
ethyl 6-bromo-2-ethyl-2-methylhexanoate
ethyl 7-bromoheptanoate
methyl 6-bromo-2-ethylhexanoate
ethyl 8-bromooctanoate When the procedure of Example 4 is followed and 4,6-diphenyl-2-pyridone is replaced by the compounds of Table VI below, then the corresponding product is prepared.

Table VI 4-(4-chlorophenyl)-6-phenyl-2-pyridone
6-(4-chlorophenyl)-4-phenyl-2-pyridone
4-(4-methoxyphenyl)-6-phenyl-2-pyridone
6-(4-methoxyphenyl)-4-phenyl-2-pyridone (m.p.= 243°–245° C.)
6-(4-trifluoromethylphenyl)-4-phenyl-2-pyridone
4,6-di(4-chlorophenyl)-2-pyridone
6-(4-methylphenyl)-4-phenyl-2-pyridone
6-(4-chlorophenyl)-4-(4-methoxyphenyl)-2-pyridone
4-(4-chlorophenyl)-6-(4-methoxyphenyl)-2-pyridone
6-phenyl-4-(4-trifluoromethylphenyl)-2-pyridone
6-phenyl-4-(3,4-methylenedioxyphenyl)-2-pyridone
4-(3-methoxyphenyl)-6-phenyl-2-pyridone
4,6-di(4-methoxyphenyl)-2-pyridone
4-(4-fluorophenyl)-6-phenyl-2-pyridone
6-(4-fluorophenyl)-4-phenyl-2-pyridone
6-(2-fluorophenyl)-4-phenyl-2-pyridone
6-(3-methoxyphenyl)-4-phenyl-2-pyridone
4-(4-methylphenyl)-6-phenyl-2-pyridone
4-(3-chlorophenyl)-6-phenyl-2-pyridone
6-(2-chlorophenyl)-4-phenyl-2-pyridone
4-(3-chlorophenyl)-6-phenyl-2-pyridone
4-(4-chlorophenyl)-6-phenyl-2-pyridone
4-phenyl-2-quinolinone
4-(4-chlorophenyl)-2-quinolinone
4-(3-chlorophenyl)-2-quinolinone
4-(2-fluorophenyl)-2-quinolinone
4-(4-fluorophenyl)-2-quinolinone
4-(3,4-dichlorophenyl)-2-quinolinone
6-chloro-4-phenyl-2-quinolinone
7-chloro-4-phenyl-2-quinolinone
(4-nitrophenyl)-2-quinolinone
4-(3-methoxyphenyl)-2-quinolinone
4-(4-methoxyphenyl)-2-quinolinone
4-(4-tolyl)-2-quinolinone
4-(3-tolyl)-2-quinolinone
7-methyl-4-phenyl-2-quinolinone
4-(4-trifluoromethylphenyl)-2-quinolinone
4-(4-dimethylaminophenyl)-2-quinolinone
methyl 4-(2-thienyl)-2-quinolinone
4-phenyl-2-pyridone
5,6-diphenyl-2-pyridone
5,6-bis-(4-methoxyphenyl)-2-pyridone
6-phenyl-2-pyridone
4,5-bis-(4-chlorophenyl)-2-pyrimidone
4,5-diphenyl-2-pyrimidone
7-methoxy-3-phenyl-2-quinolinone
4,5-bis-(4-methoxyphenyl)-2-pyrimidone When the procedure of Example 4 is followed and 4,6-diphenyl-2-pyridone and 6-bromohexanoate are replaced by the compounds of Tables V and VI above, then the corresponding product is prepared. A representative list of compounds so prepared are shown in Table VII below.

Table VII methyl 2,2-dimethyl-6-[(4,6-diphenyl-2-pyridyl)oxy]hexanoate (brown oil)
ethyl 5-[(4,6-diphenyl-2-pyridyl)oxy]pentanoate (yellowish oil)
ethyl 4-[(4,6-diphenyl-2-pyridyl)oxy]butanoate (yellowish oil).
methyl 6-[(4,6-diphenyl-2-pyridyl)oxy]hexanoate (m.p.= 57°–58° C.)
ethyl 6-{[4-(4-chlorophenyl)-6-phenyl-2-pyridyl]oxy}hexanoate (yellowish oil)
ethyl 6-{[6-(4-chlorophenyl)-4-phenyl-2-pyridyl]oxy}hexanoate (m.p.=84°–85° C.)
ethyl 6-{[4-(4-methoxyphenyl)-6-phenyl-2-pyridyl]oxy}hexanoate (yellowish solid)
ethyl 6-{[6-(4-methylphenyl)-4-phenyl-2-pyridyl]oxy}hexanoate (yellowish oil).
ethyl 6-{[6-(4-fluorophenyl)-4-phenyl-2-pyridyl]oxy}hexanoate. (yellow oil)
ethyl 6-[(4-phenyl-2-quinolyl)oxy]hexanoate
ethyl 2-methyl-6-[(4-phenyl-2-quinolyl)oxy]hexanoate
methyl 2,2-dimethyl-6-[(4-phenyl-2-quinolyl)oxy]hexanoate
ethyl 2-ethyl-2-methyl-6-[(4-phenyl-2-quinolyl)oxy]hexanoate
ethyl 7-[(4-phenyl-2-quinolyl)oxy]hexanoate
6-[4-(4-chlorophenyl)-2-quinolyl]oxy}hexanoate
ethyl 2-methyl-6-{[4-(4-chlorophenyl)-2-quinolyl]oxy}hexanoate
ethyl 2-ethyl-6-{[4-(4-chlorophenyl)-2-quinolyl]oxy}hexanoate methyl 2,2-dimethyl-6-{[4-(4-chlorophenyl)-2-quinolyl]oxy}hexanoate
methyl 2,2-dimethyl-6-{[4-(3-chlorophenyl)-2-quinolyl]oxy}hexanoate
ethyl 2,2-dimethyl-6-{[4-(2-fluorophenyl)-2-quinolyl]oxy}hexanoate
methyl 2,2-dimethyl-6-{[4-(4-fluorophenyl)-2-quinolyl]oxy}hexanoate
methyl 2,2-dimethyl-6-{[4-(3,4-dichlorophenyl)-2-quinolyl]oxy}hexanoate
methyl 2,2-dimethyl-6-[(6-chloro-4-phenyl-2-quinolyl)oxy}hexanoate
methyl 2,2-dimethyl-6-[(7-chloro-4-phenyl-2-quinolyl)oxy}hexanoate
methyl 2,2-dimethyl-6-{[4-(4-nitrophenyl)-2-quinolyl]oxy}hexanoate (m.p.=111°–112° C.,)
methyl 2,2-dimethyl-6-{[4-(3-methoxyphenyl)-2-quinolyl)oxy}hexanoate
methyl 2,2-dimethyl-6-{[4-(4-methoxyphenyl)-2-quinolyl]oxy}hexanoate (m.p.=66°–67.5° C.)
ethyl 2-methyl-6-{[4-(4-methoxyphenyl)-2-quinolyl]oxy}hexanoate
methyl 2,2-dimethyl-6-{[4-(4-tolyl)-2-quinolyl]oxy}hexanoate
methyl 2,2-dimethyl-6-[(7-methyl-4-phenyl-2-quinolyl)oxy]hexanoate
methyl 2,2-dimethyl-6-{[4-(4-trifluoromethylphenyl)-2-quinolyl]oxy}hexanoate
methyl 2,2-dimethyl-6-{[4-(2-thienyl)-2-quinolyl]oxy}hexanoate
methyl 2,2-dimethyl-6-{[4-(4-aminophenyl)-6-phenyl-2-pyridyl]oxy}hexanoate (brown-yellowish oil)
methyl 2,2-dimethyl-6-{[4-(4-aminophenyl)-2-quinolyl]oxy}hexanoate (yellow oil)
ethyl 6-[(4-phenyl-2-pyridyl)oxy]hexanoate (oil)
ethyl 6-[(4,6-diphenyl-2-pydmidyl)oxy]hexanoate (yellow solid)
ethyl 6-[(5,6-diphenyl-2-pyridyl)oxy]hexanoate
methyl 6-[(5,6-diphenyl-2-pyridyl)oxy]-2,2-dimethylhexanoate (m.p.=85°–87° C.
ethyl 8-[(5,6-diphenyl-2-pyridyl)oxy]octanoate (oil)
ethyl 6-{[5,6-bis-(4-methoxyphenyl)-2-pyridyl]oxy}hexanoate (oil)
ethyl 8-{[5,6-bis-(4-methoxyphenyl)-2-pyridyl]oxy}octanoate (oil)
ethyl 6-[(6-phenyl-2-pyridyl)oxy]hexanoate (oil)
ethyl 7-[(6-phenyl-2-pyridyl)oxy]hexanoate (oil)
methyl 6-[(6-phenyl-2-pyridyl)oxy]-2,2-dimethylhexanoate (oil)
ethyl 8-[(6-phenyl-2-pyridyl)oxy]octanoate (oil)
ethyl 6-[4,5-bis-(4-chlorophenyl)-2-pyrimidyloxy]hexanoate (oil)
ethyl 8-(4,5-diphenyl)-2-pyrimidyloxy]octanoate (yellow oil)
ethyl 6-[4.5-bis-(4-methoxyphenyl)-2-pyrimidyloxy]hexanoate (oil)
ethyl 7-[(4,6-diphenyl-2-pyridyl)oxy]heptanoate (yellowish oil)
ethyl 7-(4,5-diphenyl-2-pyrimidyloxy)heptanoate (oil)
methyl 6-(4,5-diphenyl-2-pyrimidyloxy)hexanoate (yellow solid)
ethyl 8-(7-methoxy-3-phenyl-2-quinolyloxy)octanoate (colorless oil).

EXAMPLE 5 methyl 2,2-dimethyl-7-[(4,6,diphenyl-2-pyridyl)oxy]heptanoate

The suspension obtained by mixing 4,6-diphenyl-2-pyridone (4 g), methyl 7-bromo-2-dimethylheptanoate (8.1 g) (prepared according to the method described in U.S. Pat. No. 4,714,762) and silver carbonate (2.2 g) in dimethylformamide (150 cc) is heated at 100° C., protected from light, for days. The reaction mixture is concentrated to dryness at 40° C. under reduced pressure. Excess methyl 7-bromo-2,2-dimethylheptanoate is distilled under reduced pressure (bulb distiller; 100° C. 0.1 mbar). The oily residue obtained is purified by chromatography under pressure on silica gel (30– 60 mm; eluent: n-hexane-ethyl acetate 9-1). (yellowish oil.)

When the procedure of Example 5 is followed and methyl 7-bromo-2,2-dimethylheptanoate is replaced by the compounds of Table VIII below, then the corresponding product is obtained.

Table VIII ethyl 6-bromo-2-methylhexanoate
methyl 6-bromo-2-ethylhexanoate
ethyl 6-bromo-2-ethyl-2-methylhexanoate
methyl 8-bromo-2,2-dimethyloctanoate
methyl 8-bromo-2,2-dimethyloctanoate
methyl 6-bromo-2,2-dimethylhexanoate
ethyl 6-bromohexanoate
methyl 6-bromo-2,2-dimethylhexanoate
ethyl 6-bromo-2-methylhexanoate
ethyl 8-bromooctanoate
ethyl 6-bromo-2-methylhexanoate
methyl 6-bromo-2,2-dimethylhexanoate
6-bromohexanoate
ethyl 6-bromo-2-methylhexanoate
methyl 3-bromomethylbenzoate
methyl 4-bromomethylbenzoate
methyl 6-bromo-2,2-dimethylhexanoate When the procedure of Example 5 is followed and 4,6-diphenyl-2-pyridone is replaced by the compounds of Table IX, below then the corresponding product is obtained.

Table IX 6-(4-trifluoromethylphenyl)-4-phenyl-2-pyridone
4-(4-chlorophenyl)-6-(4-methoxyphenyl)-2-pyridone
4-(2-fluorophenyl)-6-phenyl-2-pyridone
6-phenyl-4-(4-trifluoromethylphenyl)-2-pyridone
4-(3-methoxyphenyl)-6-phenyl-2-pyridone
4,6-di(4-methoxyphenyl)-2-pyridone
4-(4-fluorophenyl)-6-phenyl-2-pyridone
6-(2-fluorophenyl)-4-phenyl-2-pyridone
6-(3-methoxyphenyl)-4-phenyl-2-pyridone
4-(3,4-dichlorophenyl)-6-phenyl-2-pyridone
4-(4-methylphenyl)-6-phenyl-2-pyridone
4-(3-chlorophenyl)-6-phenyl-2-pyridone
6-(2-chlorophenyl)-4-phenyl-2-pyridone
4-(2-chlorophenyl)-6-phenyl-2-pyridone
4-(3-chlorophenyl)-6-phenyl-2-pyridone
4-(4-chlorophenyl)-6-phenyl-2-pyridone
6-(4-chlorophenyl)-4-phenyl-2-pyridone
4-(3-chlorophenyl)-6-phenyl-2-pyridone
6-(2-fluorophenyl)-4-phenyl-2-pyridone
6-(3-fluorophenyl)-4-phenyl-2-pyridone
4-(3-fluorophenyl)-6-phenyl-2-pyridone
4-(4-fluorophenyl)-6-phenyl-2-pyridone
4-(4-fluorophenyl)-6-(2-fluorophenyl)-2-pyridone
4-(3-methoxyphenyl)-6-phenyl-2-pyridone
4-(4-methylthiophenyl)-6-phenyl-2-pyridone
4-(3,4-methylenedioxyphenyl)-6-phenyl-2-pyridone
4-(3-methylphenyl)-6-phenyl-2-pyridone
4-(4-methylphenyl)-6-phenyl-2-pyridone 4-(4-dimethylaminophenyl)-6-phenyl-2-pyridone
4-(4-nitrophenyl)-6-phenyl-2-pyridone
4-phenyl-6-(2-thienyl)-2-pyridone
4-phenyl-6-(3-thienyl)-2-pyridone
4-(3-tolyl)-2-quinolinone
4-(4-nitrophenyl)-6-phenyl-2-pyridone
4-(3-nitrophenyl)-6-phenyl-2-pyridone
6-(2-chlorophenyl)-4-(3,4-methylenedioxyphenyl)-2-pyridone,
4-phenyl-3-methyl-2-quinolinone
4-(4-chlorophenyl)-2-pyridone
6-ter-butyl-4-phenyl-2-pyridone
6-methyl-4-phenyl-2-pyridone
6-cyclo-propyl-4-phenyl-2-pyridone
6-cyclo-propyl-4-phenyl-2-pyridone
6-methyl-4-phenyl-2-quinolinone
4-(2-methoxyphenyl)-2-quinolinone
6-methoxy-4-phenyl-2-quinolinone
6-phenyl-4-(3,4-dimethoxyphenyl)-2-pyridone When the procedure of Example 5 is followed and 4,6-diphenyl-2-pyridone is replaced by a compound selected from Table VI or Table IX and methyl 7-bromo-2,2-dimethylheptanoate is replaced by a compound selected from Table V or Table VIII, then the corresponding product is obtained. Representative compounds so prepared are identified in Table X below.

Table X ethyl 2-methyl-6-[(4,6-diphenyl-2-pyridyl)oxy]hexanoate (reddish oil)
methyl 2-ethyl-6-[(4,6-diphenyl-2-pyridyl)oxy]hexanoate (yellow oil)
ethyl 2-ethyl-2-methyl-6-[(4,6-diphenyl-2-pyridyl)oxy]hexanoate (yellow oil)
methyl 2,2-dimethyl-8-[(4,6-diphenyl-2-pyridyl)oxy]octanoate (yellow oil)
methyl 2,2-dimethyl-6-{[4-(4-chlorophenyl)-6-phenyl-2-pyridyl]oxy}hexanoate (yellowish oil).
methyl 2,2-dimethyl-6-{[4-(4-methoxyphenyl)-6-phenyl-2-pyridyl]oxy}hexanoate (colorless oil).
ethyl 2-methyl-6-{[4-(4-methoxyphenyl)-6-phenyl-2-pyridyl]oxy}hexanoate (colorless oil).
ethyl 6-{[4-(2-fluorophenyl)-6-phenyl-2-pyridyl]oxy}hexanoate (yellow oil)
ethyl 6-{[6-phenyl-4-(4-trifluoromethylphenyl)-2-pyridyl]oxy}hexanoate. (yellowish oil)
ethyl 6-{[4-(3-methoxyphenyl)-6-phenyl-2-pyridyl]oxy}hexanoate (colorless oil).
methyl 2,2-dimethyl-6-{[4-(3-methoxyphenyl)-6-phenyl-2-pyridyl]oxy}hexanoate (yellow oil)
ethyl 6-{[4-(4-fluorophenyl)-6-phenyl-2-pyridyl]oxy}hexanoate (yellow oil)
methyl,2,2-dimethyl-6-{[4-(4-fluorophenyl)-6-phenyl-2-pyridyl]oxy}hexanoate (yellowish oil)
ethyl 6-{[6-(2-fluorophenyl)-4-phenyl-2-pyridyl]oxy}hexanoate (colorless oil).
ethyl 6-{[4-(4-methylphenyl)-6-phenyl-2-pyridyl]oxy}hexanoate (yellowish oil).
ethyl 6-{[4-(3-chlorophenyl)-6-phenyl-2-pyridyl]oxy}hexanoate (yellowish oil).
ethyl 6-{[6-(2-chlorophenyl)-4-phenyl-2-pyridyl]oxy}hexanoate (yellowish oil).
ethyl 6-{[4-(2-chlorophenyl)-6-phenyl-2-pyridyl]oxy}hexanoate (orange oil).
ethyl 2-methyl-6-{[4-(3-chlorophenyl)-6-phenyl-2-pyridyl]oxy}hexanoate (yellow oil)
ethyl 2-methyl-6-{[4-(4-chlorophenyl)-6-phenyl-2-pyridyl]oxy}hexanoate (yellow oil).
methyl 6-{[4-(4-chlorophenyl)-6-phenyl-2-pyridyl]oxy}hexanoate (m.p.=97°–98° C.)
ethyl 2-methyl-6-{[6-(2-fluorophenyl)-4-phenyl-2-pyridyl]oxy}hexanoate (yellow oil)
methyl 2,2-dimethyl-6-{[6-(2-fluorophenyl)-4-phenyl-2-pyridyl]oxy}hexanoate (yellow oil)
ethyl 6-{[6-(3-fluorophenyl)-4-phenyl-2-pyridyl]oxy}hexanoate (colorless oil)
ethyl 6-{[4-(3-fluorophenyl)-6-phenyl-2-pyridyl]oxy}hexanoate (yellow oil)
ethyl 2-methyl-6-{[4-(4-fluorophenyl)-6-phenyl-2-pyridyl]oxy}hexanoate: (yellow oil).
ethyl 6-{[4-(4-fluorophenyl)-6-(2-fluorophenyl)-2-pyridyl]oxy}hexanoate (yellow oil)
ethyl 2-methyl-6-{[4-(3-methoxyphenyl)-6-phenyl-2-pyridyl]oxy}hexanoate (yellow oil)
ethyl 6-{[4-(4-methylthiophenyl)-6-phenyl-2-pyridyl]oxy}hexanoate (m.p.=55° C.)
ethyl 6-{[4-(3,4-methylenedioxyphenyl)-6-phenyl-2-pyridyl]oxy}hexanoate (white solid)
ethyl 2-methyl-6-{[4-(3,4-methylenedioxyphenyl)-6-phenyl-2-pyridyl]oxy} hexanoate (yellowish oil)
ethyl 6-{[4-(3-methylphenyl)-6-phenyl-2-pyridyl]oxy}hexanoate. (yellowish oil)
ethyl 2-methyl-6-{[4-(4-methylphenyl)-6-phenyl-2-pyridyl]oxy}hexanoate (yellowish oil)
ethyl 6-{[4-(4-dimethylaminophenyl)-6-phenyl-2-pyridyl]oxy}hexanoate. (yellow solid)
ethyl 6-{[4-(4-nitrophenyl)-6-phenyl-2-pyridyl]oxy}hexanoate (m.p.=75°–76° C.)
ethyl 6-{[4-phenyl-6-(2-thienyl)-2-pyridyl]oxy}hexanoate (yellow oil).
methyl 2,2-dimethyl-6-{[4-phenyl-6-(2-thienyl)-2-pyridyl]oxy}hexanoate (yellowish oil)
ethyl 6-{[4-phenyl-6-(3-thienyl)-2-pyridyl]oxy}hexanoate. (yellow oil)
methyl 2,2-dimethyl-6-{[4-phenyl-6-(3-thienyl)-2-pyridyl]oxy}hexanoate (yellowish oil)
ethyl 8-[(4-phenyl-2-quinolyl)oxy]octanoate.
methyl 2,2-dimethyl-6-{[4-(3-tolyl)-2-quinolyl]oxy}hexanoate.
methyl 2,2-dimethyl-6-{[4-(4-dimethylaminophenyl)-2-quinolyl]oxy}hexanoate
ethyl 6-{[4-(4-nitrophenyl)-6-phenyl-2-pyridyl]oxy}hexanoate
ethyl 6-{[4-(4-aminophenyl)-6-phenyl-2-pyridyl]oxy}hexanoate
ethyl 2-methyl-6-{[4-(4-nitrophenyl)-6-phenyl-2-pyridyl]oxy}hexanoate (yellow oil)
ethyl 2-methyl-6-{[4-(4-aminophenyl)-6-phenyl-2-pyridyl]oxy}hexanoate (yellow oil)
methyl 2,2-dimethyl-6-{[4-(4-nitrophenyl)-6-phenyl-2-pyridyl]oxy} hexanoate. (m.p.=90°–91° C.)
methyl 2,2-dimethyl-6-{[4-(4-nitrophenyl)-6-phenyl-2-pyridyl]oxy}hexanoate (m.p.=90°–91° C.)
ethyl 6-{[4-(3-nitrophenyl)-6-phenyl-2-pyridyl]oxy}hexanoate (yellow oil)
ethyl 6-{[6-(2-chlorophenyl)-4-(3,4-methylenedioxyphenyl)-2-pyridyl]oxy}-2-methylhexanoate (oil).
ethyl 6-{[6-(2-chlorophenyl)-4-phenyl-2-pyridyl]oxy}-2-methylhexanoate (oil)
methyl 2,2-dimethyl-6-[(3-methyl-4-phenyl-2-quinolyl)oxy]hexanoate (oil)
methyl 6-[(4-phenyl-2-pyridyl)oxy]-2,2-dimethylhexanoate (oil)

methyl 6-{[4-(4-chlorophenyl)-2-pyridyl]oxy}-2,2-dimethylhexanoate (oil)
ethyl 6-[(6-ter-butyl-4-phenyl-2-pyridyl)oxy]hexanoate (oil)
methyl 6-[(6-ter-butyl-4-phenyl-2-pyridyl)oxy]-2,2-dimethylhexanoate (oil)
ethyl 6-[(6-methyl-4-phenyl-2-pyridyl)oxy]hexanoate (oil)
methyl 6-[(6-methyl-4-phenyl-2-pyridyl)oxy]-2,2-dimethylhexanoate (oil)
ethyl 6-[(6-cyclo-propyl-4-phenyl-2-pyridyl)oxy]hexanoate (oil)
methyl 6-[(6-cyclo-propyl-4-phenyl-2-pyridyl)oxy]-2,2-dimethylhexanoate (oil)
methyl 6-[(6-methyl-4-phenyl-2-quinolyl)oxy]-2,2-dimethylhexanoate (oil)
methyl 6-{4-(2-methoxyphenyl)-2-quinolyl]oxy}-2,2-dimethylhexanoate (oil)
ethyl 6-[(6-methoxy-4-phenyl-2-quinolyl)oxy]hexanoate (oil)
ethyl 6-{[6-phenyl-4-(3,4-dimethoxyphenyl)-2-pyridyl] oxy}hexanoate (oil)
4-[(4,6-diphenyl-2-pyridyl)oxymethyl]benzoate (m.p.=115° C.)
methyl 3-[(4,6-diphenyl-2-pyridyl)oxymethyl]benzoate (oil)
methyl 6-[(4,6-diphenyl-2-pyrimidyl)oxy]-2,2-dimethylhexanoate (yellow solid).

EXAMPLE 6

6-[(4,6-diphenyl-2-pyridyl)oxy]hexanoic acid

To a solution of ethyl 6-[(4,6-diphenyl-2-pyridyl)oxy] hexanoate (3.7 g) in ethanol (100 cc) are added sodium hydroxide pellets (0.6 g). The reaction mixture is refluxed for 1 hour and then concentrated to dryness under reduced pressure. The residue obtained is dissolved in distilled water (150 cc). The pH of the aqueous phase is brought to about 5 by addition of a 2N aqueous solution of hydrochloric acid. It is then extracted with methylene chloride (3×50 cc). The organic phases are combined, washed with distilled water (3×50 cc), dried over sodium sulphate and concentrated to dryness at 40° C. under reduced pressure. The solid residue obtained is purified by recrystallization in an n-hexane-ethyl acetate (10-1) mixture (55 cc). (white crystals; m.p.= 87°–88° C.)

When the procedure of Example 6 is followed and 6-[(4, 6-diphenyl- 2-pyridyl)oxy]hexanoate is replaced by a compound selected from, Table VII or Table X, then the corresponding product is prepared. , Representative compounds so prepared are identified in Table XI below.

Table XI 2,2-dimethyl-6-[(4,6-diphenyl-2-pyridyl)oxy]hexanoic acid (m.p.=109°–111° C.)
7-[(4,6-diphenyl-2-pyridyl)oxy]heptanoic acid (white crystals; m.p.=104°–106° C.)
5-[(4,6-diphenyl-2-pyridyl)oxy]pentanoic acid (m.p.= 160°–163° C.)
4-[(4,6-diphenyl-2-pyridyl)oxy]butanoic acid (m.p.= 125°–128° C.)
2,2-dimethyl-7-[(4,6-diphenyl-2-pyridyl)oxy]heptanoic acid (m.p.=98°–99° C.)
2-methyl-6-[(4,6-diphenyl-2-pyridyl)oxy]hexanoic acid (m.p.=87°–88° C.)
2-ethyl-6-[(4,6-diphenyl-2-pyridyl)oxy]hexanoic acid (m.p.=115° C.)
2-ethyl-2-methyl-6-[(4,6-diphenyl-2-pyridyl)oxy]hexanoic acid (m.p.=119°–120° C.)
2,2-dimethyl-8-[(4,6-diphenyl-2-pyridyl)oxy]octanoic acid (m.p.=80° C.)
6-{[4-(4-chlorophenyl)-6-phenyl-2-pyridyl]oxy}hexanoic acid (m.p.=108°–110° C.)
2,2-dimethyl-6-{[4-(4-chlorophenyl)-6-phenyl-2-pyridyl] oxy}hexanoic acid (m.p.=101°–103° C.)
6-{[6-(4-chlorophenyl)-4-phenyl-2-pyridyl]oxy}hexanoic acid (m.p.=103°–105° C.)
6-{[4-(4-methoxyphenyl)-6-phenyl-2-pyridyl] oxy}hexanoic acid (m.p.=74°–76° C.)
2,2-dimethyl-6-{[4-(4-methoxyphenyl)-6-phenyl-2-pyridyl] oxy}hexanoic acid (m.p.=108.5° C.)
2-methyl-6-{[4-(4-methoxyphenyl)-6-phenyl-2-pyridyl] oxy}hexanoic acid (m.p.=86° C.) ,
6-{[6-(4-methoxyphenyl)-4-phenyl-2-pyridyl] oxy}hexanoic acid (m.p.=88°–90° C.)
6-{[6-(4-trifluoromethylphenyl)-4-phenyl-2-pyridyl] oxy}hexanoic acid (m.p.=113°–114° C.)
6-{[4,6-di(4-chlorophenyl)-2-pyridyl]oxy}hexanoic acid (m.p.=84°–86° C.)
6-{[6-(4-methylphenyl)-4-phenyl-2-pyridyl]oxy}hexanoic acid (m.p.=76°–78° C.).
6-{[6-(4-chlorophenyl)-4-(4-methoxyphenyl)-2-pyridyl] oxy}hexanoic acid (m.p.=110°–112° C.)
6-{[4-(4-chlorophenyl)-6-(4-methoxyphenyl)-2-pyridyl] oxy}hexanoic acid (m.p.=129°–130° C.)
6-{[4-(2-fluorophenyl)-6-phenyl-2-pyridyl]oxy}hexanoic add (m.p.=100°–1 01° C.)
6-{[6-phenyl-4'(4-trifluoromethylphenyl)-2-pyridyl] oxy}hexanoic add (m.p.=90°–91° C.)
6-{[4-(3-methoxyphenyl)-6-phenyl-2-pyridyl] oxy}hexanoic acid (m.p.=115°–116° C.)
2,2-dimethyl-6-{[4-(3-Methoxyphenyl)-6-phenyl-2-pyridyl]oxy}hexanoic acid (m.p.=89° C.)
6-{[4,6-di(4-methoxyphenyl)-2-pyridyl]oxy}hexanoic acid (m.p.=118° C.)
6-{[4-(4-fluorophenyl)-6-phenyl-2-pyridyl]oxy}hexanoic acid (m.p.=95°–96° C.)
2,2-dimethyl-6-{[4-(4-fluorophenyl)-6-phenyl-2-pyridyl] oxy}hexanoic acid (m.p.=119°–121° C.)
6-{[6-(4-fluorophenyl)-4-phenyl-2-pyridyl]oxy}hexanoic acid (m.p.=94°–95° C.)
6-{[6-(2-fluorophenyl)-4-phenyl-2-pyridyl]oxy}hexanoic acid (m.p.=86°–87° C.)
6-{[6-(3-methoxyphenyl)-4-phenyl-2-pyridyl] oxy}hexanoic acid (m.p.=91° C.)
6-{[4-(3,4-dichlorophenyl)-6-phenyl-2-pyridyl] oxy}hexanoic acid (m.p.=101° C.)
6-{[4-(4-methylphenyl)-6-phenyl-2-pyridyl]oxy}hexanoic acid (m.p.=101 102° C.)
6-{[4-(3-chlorophenyl)-6-phenyl-2-pyridyl]oxy}hexanoic acid (m.p.=61°–63° C.)
sodium 6-{[6-(2-chlorophenyl)-4-phenyl-2-pyridyl] oxy}hexanoate (m.p.=255° C.dec.).
6-{[4-(2-chlorophenyl)-6-phenyl-2-pyridyl]oxy}hexanoic acid (m.p.=73° C. dec.)
2-methyl-6-{[4-(3-chlorophenyl)-6-phenyl-2-pyridyl] oxy}hexanoic acid (m.p.=55°–57° C.)
2-methyl-6-{[4-(4-chlorophenyl)-6-phenyl-2-pyridyl] oxy}hexanoic acid (m.p.=97°–98° C.)
2,2-dimethyl-6-{[4-(3-chlorophenyl)-6-phenyl-2-pyridyl] oxy}hexanoic acid (m.p.=118° C.) .
2-methyl-6-{[6-(2-fluorophenyl)-4-phenyl-2-pyridyl] oxy}hexanoic acid (m.p.=87° C.)

2,2-dimethyl-6-{[6-(2-fluorophenyl)-4-phenyl-2-pyridyl]oxy}hexanoic acid (m.p.=133° C.)
6-{[6-(3-fluorophenyl)-4-phenyl-2-pyridyl]oxy}hexanoic acid (m.p.=93° C.)
6-{[4-(3-fluorophenyl)-6-phenyl-2-pyridyl]oxy}hexanoic add (m.p.=101° C.)
2-methyl-6-{[4-(4-fluorophenyl)-6-phenyl-2-pyridyl]oxy}hexanoic acid (m.p.=101° C.)
6-{[4-(4-fluorophenyl)-6-(2-fluorophenyl)-2-pyridyl]oxy}hexanoic acid (m.p.=86° C.)
2-methyl-6-{[4-(3-methoxyphenyl)-6-phenyl-2-pyridyl]oxy}hexanoic acid (m.p.=103° C.)
6-{[4-(4-methylthiophenyl)-6-phenyl-2-pyridyl]oxy}hexanoic acid . (m.p.=104.5° C.)
6-{[4-(3, 4-methylenedioxyphenyl)-6-phenyl-2-pyridyl]oxy}hexanoic acid (m.p.=124°–126° C.)
2-methyl-6-{[4-(3,4-methylenedioxyphenyl)-6-phenyl-2-pyridyl]oxy}hexanoic acid (m.p.=123°–125° C.)
6-{[4-(3-methylphenyl)-6-phenyl-2-pyridyl]oxy}hexanoic acid (m.p.=67° C.)
2,2-dimethyl-6-{[4-(3,4-methylenedioxyphenyl)-6-phenyl-2-pyridyl]oxy} hexanoic acid (m.p.=166°–167° C.)
2-methyl-6-{[4-(4-methylphenyl)-6-phenyl-2-pyridyl]oxy}hexanoic acid (m.p.=83°–85° C.)
6-{[4-(4-dimethylaminophenyl)-6-phenyl-2-pyridyl]oxy}hexanoic acid (m.p.=159° C.)
6-{[4-(4-nitrophenyl)-6-phenyl-2-pyridyl]oxy}hexanoic acid (m.p.=118°–119° C.)
6-{[4-phenyl-6-(2-thienyl)-2-pyridyl]oxy}hexanoic acid (m.p.=71°–73° C.)
2,2-dimethyl-6-{[4-phenyl-6-(2-thienyl)-2-pyridyl]oxy}hexanoic acid (m.p.=121°–122° C.)
6-{[4-phenyl-6-(3-thienyl)-2-pyridyl]oxy}hexanoic acid (m.p.=109°–110° C.)
2,2-dimethyl-6-{[4-phenyl-6-(3-thienyl)-2-pyridyl]oxy}hexanoic acid (m.p.=104°–106° C.)
6-[(4-phenyl-2-quinolyl)oxy]hexanoic acid (m.p.=80°–81° C.)
2-methyl-6-[(4-phenyl-2-quinolyl)oxy]hexanoic add (m.p.=81° C.)
2,2-dimethyl-6-[(4-phenyl-2-quinolyl)oxy]hexanoic acid (m.p.=118°–120° C.)
2-ethyl-2-methyl-6-[(4-phenyl-2-quinolyl)oxy]hexanoic acid (colorless oil; I.R. (KBr): 1697 cm.$^{-1}$.)
7-[(4-phenyl-2-quinolyl)oxy]heptanoic acid (m.p.=62°–65° C.)
8-[(4-phenyl-2-quinolyl)oxy]octanoic acid (m.p.=68° C.)
6-{[4-(4-chlorophenyl)-2-quinolyl]oxy}hexanoic acid. (m.p.=75°–77° C.)
2-methyl-6-{[4-(4-chlorophenyl)-2-quinolyl]oxy}hexanoic acid (m.p.=103°–104° C.)
2-ethyl-6-{[4-(4-chlorophenyl)-2-quinolyl]oxy}hexanoic acid (m.p.=122°–123° C.)
2,2-dimethyl-6-{[4-(4-chlorophenyl)-2-quinolyl]oxy}hexanoic acid (m.p.=110°–111° C.)
2,2-dimethyl-6-{[4-(3-chlorophenyl)-2-quinolyl]oxy}hexanoic acid (m.p.=115° C.)
2-dimethyl-6-{[4-(2-fluorophenyl)-2-quinolyl]oxy}hexanoic acid (m.p.=91° C.)
2,2-dimethyl-6-{[4-(4-fluorophenyl)-2-quinolyl]oxy}hexanoic acid : (m.p.=78°–79° C.)
2,2-dimethyl-6-{[4-(3,4-dichlorophenyl)-2-quinolyl]oxy}hexanoic acid (m.p.=163°–164° C.)
2,2-dimethyl-6-[(6-chloro-4-phenyl-2-quinolyl)oxy}hexanoic acid (m.p.=141° C.)
2,2-dimethyl-6-[(7-chloro-4-phenyl-2-quinolyl)oxy]hexanoic acid (m.p.=102° C.)
2,2-dimethyl-6-{[4-(4-nitrophenyl)-2-quinolyl]oxy}hexanoic acid (m.p.=85°–92° C.)
2,2-dimethyl-6-{[4-(3-methoxyphenyl)-2-quinolyl)oxy}hexanoic acid [yellowish oil; I.R. (KBr)1699 cm.$^{-1}$]
2,2-dimethyl-6-{[4-(4-methoxyphenyl)-2-quinolyl]oxy}hexanoic acid (m.p.=108°–109° C.)
2-methyl-6-{[4-(4-methoxyphenyl)-2-quinolyl]oxy}hexanoic acid (m.p.=80°–81° C.)
2,2-dimethyl-6-{[4-(3-tolyl)-2-quinolyl]oxy}hexanoic acid (m.p.=78°–79° C.)
2,2-dimethyl-6-{[4-(4-tolyl)-2-quinolyl]oxy}hexanoic acid (m.p.=93°–94° C.)
2,2-dimethyl-6-[(7-methyl-4-phenyl-2-quinolyl)oxy]hexanoic acid (colorless oil).
2,2-dimethyl-6-{[4-(4-trifluoromethylphenyl)-2-quinolyl]oxy}hexanoic add (m.p.=128°–129° C.)
2,2-dimethyl-6-{[4-(4-dimethylaminophenyl)-2-quinolyl]oxy}hexanoic acid (m.p.=121°–122° C.)
2,2-dimethyl-6-{[4-(2-thienyl)-2-quinolyl]oxy}hexanoic acid (m.p.=132°–134° C.)
2-methyl-6-{[4-(4-aminophenyl)-6-phenyl-2-pyridyl]oxy}hexanoic acid (m.p.=134°–136° C.)
6-{[4-(4-aminophenyl)-6-phenyl-2-pyridyl]oxy}hexanoic acid (m.p.=131°–133° C.)
2,2-dimethyl-6-{[4-(4-aminophenyl)-6-phenyl-2-pyridyl]oxy}hexanoic acid (m.p.=123°–125° C.)
6-{[4-(4-methylaminophenyl)-6-phenyl-2-pyridyl]oxy}hexanoic acid (m.p.=115°–117° C.)
6-{[4-(4-isopropylaminophenyl)-6-phenyl-2-pyridyl]oxy}hexanoic acid (m.p.=101° C.)
6-{[4-(4-methylaminophenyl)-6-phenyl-2-pyridyl]oxy}-2,2-dimethylhexanoic acid (m.p.=144° C.)
6-{[6-(2-chlorophenyl)-4-(3,4-methylenedioxyphenyl)-2-pyridyl]oxy}-2-methyl hexanoic acid. (m.p.=109° C.).
6-{[6-(2-chlorophenyl)-4-phenyl-2-pyridyl]oxy}-2-methylhexanoic acid (m.p.=89° C.)
2,2-dimethyl-6-[(3-methyl-4-phenyl-2-quinolyl)oxy]hexanoic acid (m.p.=148°–149° C.)
2,2-dimethyl-6-[(4-phenyl-2-quinolyl)amino]hexanoic acid (m.p.=176°–177° C.)
2,2-dimethyl-6-[(4-phenyl-2-quinolyl)thio]hexanoic acid (m.p.=99°–100° C.)
6-[(4-phenyl-2-pyridyl)oxy]hexanoic acid (m.p.=54°–56° C.)
6-[(4-phenyl-2-pyridyl)oxy]-2,2-dimethylhexanoic acid (m.p.=121.5° C.)
6-{[4-(4-chlorophenyl)-2-pyridyl]oxy}-2,2-dimethylhexanoic acid (m.p.=88°–90° C.)
6-[(6-ter-butyl-4-phenyl-2-pyridyl)oxy]hexanoic acid (m.p.=71°–73° C.)
6-[(6-ter-butyl-4-phenyl-2-pyridyl)oxy]-2,2-dimethylhexanoic acid (m.p.=82°–84° C.)
6-[(6-methyl-4-phenyl-2-pyridyl)oxy]hexanoic acid (m.p.=67°–69° C.)
6-[(6-methyl-4-phenyl-2-pyridyl)oxy]-2,2-dimethylhexanoic acid (m.p.=114°–116° C.)
6-[(6-cyclopropyl-4-phenyl-2-pyridyl)oxy]hexanoic acid (m.p.=86°–88° C.)
6-[(6-cyclopropyl-4-phenyl-2-pyridyl)oxy]-2,2-dimethylhexanoic acid (m.p.=90° C.)
6-[(6-methyl-4-phenyl-2-quinolyl)oxy]-2,2-dimethylhexanoic acid (m.p.=
6-{[4-(2-methoxyphenyl)-2-quinolyl]oxy}-2,2-dimethylhexanoic acid (m.p.=152° C.)
6-[(6-methoxy-4-phenyl-2-quinolyl)oxy]hexanoic acid (m.p.=108°–110° C.)

6-{[6-phenyl-4-(3,4-dimethoxyphenyl)-2-pyridyl]oxy}hexanoic acid (m.p.=103° C.)
6-{[6-phenyl-4-(4-carboxyphenyl)-2-pyridyl]oxy}hexanoic acid (m.p.=166°–168° C.)
6-{[6-phenyl-4-(3,5-dimethoxyphenyl)-2-pyridyl]oxy}hexanoic acid (m.p.=99° C.)
4-[(4,6-diphenyl-2-pyridyl)oxymethyl]benzoic acid (m.p.=203° C.)
3-[(4,6-diphenyl-2-pyridyl)oxymethyl]benzoic add (m.p.=174° C.)
N-[4-(4,6-diphenyl-2-pyridyloxy)butanoyl]glycine (m.p.=182° C.)
6-[(4,6-diphenyl-2-pydmidyl)oxy]hexanoic acid (m.p.=104°–105° C.)
6-[(4,6-diphenyl-2-pydmidyl)oxy]-2,2-dimethylhexanoic acid. (m.p.=127°–129° C.)
6-[(5,6-diphenyl-2-pyridyl)oxy]hexanoic acid (m.p.=141°–142° C.)
6-[(5,6-diphenyl-2-pyridyl)oxy]-2,2-dimethylhexanoic acid (m.p.=116°–117° C.)
sodium 8-[(5,6-diphenyl-2-pyridyl)oxy]octanoate (IR: 1562 cm$^{-1}$)
6-{[5,6-bis-(4-methoxyphenyl)-2-pyridyl]oxy}hexanoic acid (m.p.=98° C.)
6-{[5,6-bis-(4-methoxyphenyl)-2-pyridyl]oxy}octanoic acid (m.p.=107° C.)
6-[(6-phenyl-2-pyridyl)oxy]hexanoic acid (m.p.=63° C.)
7-[(6-phenyl-2-pyridyl)oxy]heptanoic acid (m.p.=55° C.)
6-[(6-phenyl-2-pyridyl)oxy]-2,2-dimethylhexanoic acid (m.p.=74°–75° C.)
sodium 8-[(6-phenyl-2-pyridyl)oxy]octanate (I R: 1563 cm$^{-1}$)
6-[4,5-bis-(4-chlorophenyl)-2-pyrimidyloxy]hexanoic acid (m.p.=153° C.)
2,2-dimethyl-8-(4,5-diphenyl-2-pyrimidylthio)octanoic acid (m.p.=109° C.)
9-(4,5-diphenyl-2-pyrimidylthio)nonanoic acid (m.p.=90°–92° C.)
8-(4,5-diphenyl-2-pyrimidyloxy)octanoic acid (m.p.=106° C.)
6-[4,5-bis-(4-methoxyphenyl)-2-pyrimidyloxy]hexanoic acid (m.p.=142°–143° C.)
6-(4,5-diphenyl-2-pyrimidyloxy)heptanoic acid (m.p.=178°–80° C.)
6-(4,5-diphenyl-2-pyrimidyloxy)hexanoic acid (m.p.=141°–142° C.)
6-(4,5-diphenyl-2-pyrimidylthio)hexanoic acid (m.p.=103°–105° C.)
sodium 8-(4,5-diphenyl-2-pyrimidylthio)octanoate (IR: 1562 cm$^{-1}$)
sodium 8-(7-methoxy-3-phenyl-2-quinolylthio)octanoate (IR: 1562 cm$^{-1}$)
sodium 8-(7-methoxy-3-phenyl-2-quinolyloxy)octanoate (IR:1564 cm$^{-1}$)
sodium 8-(4-phenyl-2-quinazolylthio)octanoate (IR: 1563 cm$^{-1}$)
sodium 8-[(4-phenyl-2-quinolyl)thio]octanoate (IR:1563 cm$^{-1}$).

EXAMPLE 7

6-[4,6-diphenyl-2-pyridyl)oxy]hexanonitrile

The procedure of Example 4 is followed using 4,6-diphenyl-2-pyridone (6.18 g) and 6-bromohexanonitrile (6.60 g) in place of 6-bromohexanoate, silver carbonate (6.89 g) and toluene (300 cc) and the reaction mixture is refluxed for 72 hours. The material formed is purified by chromatography under pressure on silica gel (30–60 mm; eluent: n-hexane-ethyl acetate 9.5–0.5) to obtain 6-[(4,6-diphenyl-2-pyridyl)oxy]hexanonitrile as a white solid which is used directly in subsequent reactions.

When the procedure of Example 7 is followed and 4,6-diphenyl-2-pyridone is replaced by a compound selected from Table VI or Table II, then: the corresponding compound is prepared.

Similarly, as described in Example 7, when the procedure of Example 4 is followed and 6-bromohexanonitrile or 6-bromo-2,2-dimethylhexanonitrile are used in place of the ethyl ester, and are reacted with compounds selected from Table VI, then the corresponding compound is prepared. Representative compounds so prepared are described below in Table XIA.

Table XIA 2,2-dimethyl-6-[(4,6-diphenyl-2-pyridyl)oxy]hexanonitrile. (m.p.=71° C.)
6-[(4-phenyl-2-quinolyl)oxy]hexanonitrile (yellowish oil)
2,2-dimethyl-6-[(4-phenyl-2-quinolyl)oxy]hexanonitrile (m.p.=35° C.)
2,2-dimethyl-6-{[4-(4-chlorophenyl)2-quinolyl]oxy}hexanonitrile (m.p.=29° C.)
6-{[4-(4-chlorophenyl)2-quinolyl]oxy}hexanonitrile (m.p.=32° C.)
6-{[6-phenyl-4-(3,4-methylenedioxyphenyl)2-pyridyl]oxy}hexanonitrile (m.p.=108° C.)
6-{[6-phenyl-4-(3,4-methylenedioxyphenyl)2-pyridyl]oxy}-2,2-dimethyl hexanonitrile (m.p.=108° C.).

EXAMPLE 8

6-[(4,6-diphenyl-2-pyridyl)oxy)hexanamide

Dry hydrochloric acid is bubbled for 4 hours in a solution of 6-[(4,6-diphenyl-2-pyridyl)oxy]hexanonitrile (2.5 g) in formic acid (98–100%), (1.1 cc). The reaction mixture is then taken up in ethyl acetate (100 cc). The organic phase is washed with 1N sodium hydroxide, dried over sodium sulphate and concentrated to dryness at 40° C. under reduced pressure. The solid residue obtained is purified by recrystallization in toluene to obtain 6-[(4,6-diphenyl-2 -pyridyl)oxy]hexanamide as white crystals. (m.p.=118°–120° C.)

When the procedure of Example 8 is followed and 6-[(4,6-diphenyl-2-pyridyl)oxy]hexanonitrile is replaced by a compound prepared according to Example 7, such as those Identified in Table XIA, then the corresponding product is prepared.

EXAMPLE 9

5-{[5-(4,6-diphenyl-2-pyridyl)oxy]pentyl}-[1H]-tetrazole

To a solution of 6-[(4,6-diphenyl-2-pyridyl)oxy]hexanonitrile (5 g) in dimethylformamide (50 cc), are added sodium nitride (3.8 g) and ammonium chloride (3.1 g). The reaction mixture is heated at 120° C. for 96 hours and then taken up in distilled water (100 cc). After extraction with ethyl acetate (100 cc), the organic phase is washed with distilled water (2×50 cc), dried over sodium sulphate and concentrated to dryness, at 40° C., under reduced pressure. The residue thus obtained is purified by chromatography under pressure on silica gel (30–60 mm; n-hexane-ethyl acetate 1-1) and then by recrystallization in toluene to obtain 5-{[5-(4,6-diphenyl-2-pyridyl)oxy]pentyl}-[1H]-tetrazole as white crystals. (m.p.=144°–145° C.)

When the procedure of Example 9 is followed and 6-[(4,6-diphenyl-2-pyridyl)oxy]hexanonitrile is replaced by a compound prepared according to Example 7, then the representative compounds of Table XII below are prepared.

Table XII

5-{1,1-dimethyl-5-[(4,6-diphenyl-2-pyridyl)oxy]pentyl}-[1H]-tetrazole (m.p.=160°–162° C.)
5-{5-[(4-phenyl-2-quinolyl)oxy]pentyl}-[1H]-tetrazole (m.p.=134° C.)
5-{1,1-dimethyl-5-[(4-phenyl-2-quinolyl)oxy]pentyl}-[1H]-tetrazole (m.p.=170°–172° C.)
5-{1,1-dimethyl-5-{[4-(4-chlorophenyl)-2-quinolyl]oxy}pentyl}-[1H]-tetrazole. (m.p.=165°–167° C.)
5-{5-{[4-(4-chlorophenyl)-2-quinolyl]oxy}pentyl}-[1H]-tetrazole (m.p.=92°'94° C.)

EXAMPLE 10

5-{5-{[6-phenyl-4-(3,4-methylenedioxyphenyl)-2-pyridyl]oxy}pentyl}-1H-tetrazole

By using a similar procedure to that described in example 9 but with 2.4 g 6-{[6-phenyl-4-(3,4-methylenedioxyphenyl)-2-pyridyl]oxy}hexanonitrile, 1.65 g of sodium azide, 1.3 g of triethylamine hydrochloride (in place of ammonium chloride) and 90 cc of N-methylpyrrolidone (in place of dimethylformamide) as the starting material (70 hours; 150° C.), and after purification by flash chromatography on silica gel (30–60mm; eluent: ethyl acetate) and recristallization from 18 cc of acetonitrile gives 5-{5-{[6-phenyl-4-( 3,4-methylenedioxyphenyl)-2-pyridyl]oxy}pentyl }-1H-tetrazole (m.p.=150° C.)

When the procedure of Example 10 is followed but using 5-{6-{[6 -phenyl-4-(3,4-methylenedioxyphenyl)-2-pyridyl]oxy}-2-methyl-2-hexanonitrile then the product prepared is 5-{6-{[6-phenyl-4-(3,4-methylenedioxyphenyl)-2-pyridyl]-oxy}-2-methyl-2-hexyl}-1H-tetrazole. (m.p.=198° C.)

EXAMPLE 11

3-[(4,6-diphenyl-2-pyridyl)oxy]-1-propanol

The procedure in Example 4 is followed but using 4,6-diphenyl-2-pyridone (15 g), freshly distilled 3-bromo-1-propanol (16.5 cc), silver carbonate (8.4 g) and toluene (600 cc). The reaction mixture is refluxed for 144 hours. The product is purified by chromatography under pressure on silica gel (30– 60 mm; eluent: n-hexane-ethyl acetate 7-3). (white solid; m.p.=94° C.)

EXAMPLE 12 sodium 2-{3-[(4,6-diphenyl-2-pyridyl)oxy]propyloxy}acetate

To potassium tert-butylate (5.52 g) in tert-butanol (60 cc) heated to 100° C. is added, in the form of a homogeneous solid, a mixture of 3-[(4,6-diphenyl- 2-pyridyl)oxy]-1-propanol (5 g) and potassium 2-bromoacetate (4.35 g). The addition is carried out in 1 hour. The reaction mixture is then heated for 48 hours at 100° C. and then poured in iced water (100 g). The pH of the aqueous phase is brought to 5 by addition of 1N hydrochloric acid. The mixture is then extracted with dichloromethane (3×50 cc) after saturating the aqueous phase with sodium chloride. The combined organic phases are dried over sodium sulphate and concentrated to dryness at 40° C. under reduced pressure. The oily residue obtained is purified by chromatography under pressure on silica gel (30–60 mm; eluent: n-hexane-diethyl ether 65-35 and then 40-60 and then diethyl ether-methanol;9-1). The white solid obtained, taken up in acetone (5 cc), is treated with sodium hydroxide pellets (0.19 g) and distilled water (1.cc). The mixture is stirred for 60 hours at room temperature. The precipitate obtained is filtered, washed with ethyl ether and dried at 40° C. under reduced pressure. (white solid; m.p.=285°–288° C.)

EXAMPLE 13 ethyl 6-{[4-(4-aminophenyl)-6-phenyl-2-pyridyl]oxy}hexanoate

The yellow suspension obtained by mixing ethyl 6-{[4-(4-nitrophenyl)- 6-phenyl-2-pyridyl]oxy}hexanoate (5.3 g), stannous chloride (11.6 g) in ethanol (100 cc) is heated at 70° C. for 2 hours and 30 minutes under inert atmosphere. The clear brown solution thus obtained is concentrated to dryness under reduced pressure. The residue obtained is taken up in distilled water (100 cc). The pH of this aqueous phase is brought to 6 by addition of sodium hydrogenocarbonate. The solution is then extracted with ethyl acetate (3×200 cc). The organic phases are combined, washed with distilled water (3×50 cc), dried over sodium sulphate and concentrated to dryness at 40° C. under reduced pressure. The residue obtained is purified by chromatography under pressure on silica gel (30–60 mm; eluent: n-hexane-ethyl acetate 7-3). (yellowish oil).

When the procedure of Example 13 is followed and ethyl 6-{[4-(4 -nitrophenyl)-6-phenyl-2-pyridyl]oxy}hexanoate is replaced by a compound selected from Table XIII below, then the corresponding compound of Table XIV below is prepared.

Table XIII ethyl 2-methyl-6-{[4-(4-nitrophenyl)-6-phenyl-2-pyridyl]oxy}hexanoate. (yellow oil)
ethyl 2-methyl-6-{[4-(3-nitrophenyl)-6-phenyl-2-pyridyl]oxy}hexanoate.
methyl 2,2-dimethyl-6-{[4-(4-nitrophenyl)-6-phenyl-2-pyridyl]oxy} hexanoate. (m.p.90°–91° C.)
methyl 2,2-dimethyl-6-{[4-(4-nitrophenyl)-2-quinolyl]oxy}hexanoate
methyl 6-{[4-(3-nitrophenyl)-6-phenyl-2-pyridyl]oxy}hexanoate (yellow oil)

Table XIV ethyl 2-methyl-6-{[4-(4-aminophenyl)6-phenyl-2-pyridyl]oxy}hexanoate (yellow oil)
ethyl 2-methyl-6-{[4-(3-aminophenyl)-6-phenyl-2-pyridyl]oxy}hexanoate.
methyl 2,2-dimethyl-6-{[4-(4-aminophenyl)-6-phenyl-2-pyridyl]oxy}hexanoate (brown-yellowish oil)
methyl 2,2-dimethyl-6-{[4-(4-aminophenyl)-2-quinolyl]oxy}hexanoate (yellow solid)
methyl 6-{[4-(3-aminophenyl)-6-phenyl-2-pyridyl]oxy}hexanoate (yellow oil)

EXAMPLE 14

6-{[4-(4-aminophenyl)-6-phenyl-2-pyridyl]oxy}hexanoic acid

The procedure in Example 4 is followed but using ethyl 6-{[4-(4-aminophenyl)-6-phenyl-2-pyridyl]-oxy}hexanoate (3.9 g), potassium hydroxide pellets (0.81 g) dissolved in distilled water (10 cc), and ethanol (150 cc). The reaction mixture is refluxed for 2 hours. The product is purified by recrystallization in toluene (70 cc) to obtain 6-{[4-(4-aminophenyl)-6-phenyl-2-pyridyl] oxy}hexanoic acid as yellowish crystals; (m.p.=131°–133° C.)

When the procedure of Example 14 is followed and 6-{[4-(4-aminophenyl)-6-phenyl-2-pyridyl]-oxy}hexanoate is replaced by a compound selected from Tables XIII or XIV then the corresponding compound of Table XV below is prepared.

Table XV 2-methyl-6-{[4-(4-nitrophenyl)-6-phenyl-2-pyridyl] oxy}hexanoic acid 2-methyl-6-{[4-(3-nitrophenyl)-6-phenyl-2-pyridyl] oxy}hexanoic acid 2,2-dimethyl-6-{[4-(4-nitrophenyl)-6-phenyl-2-pyridyl] oxy}hexanoic acid 2,2-dimethyl-6-{[4-(4-nitrophenyl)-2-quinolyl] oxy}hexanoic acid (m.p.=150°–151° C.)

6-{[4-(3-nitrophenyl)-6-phenyl-2-pyridyl]oxy}hexanoic acid 2-methyl-6-{[4-(4-aminophenyl)-6-phenyl-2-pyridyl] oxy}hexanoic acid (m.p.=134°–136° C.)

2-methyl-6-{[4-(3-aminophenyl)-6-phenyl-2-pyridyl] oxy}hexanoic acid 2,2-dimethyl-6-{[4-(4-aminophenyl)-6-phenyl-2-pyridyl] oxy}hexanoic acid, (m.p.=123°–125° C.)

2,2-dimethyl-6-{[4-(4-aminophenyl)-2-quinolyl] oxy}hexanoic acid (m.p.=150°–151° C.)

6-{[4-(3-aminophenyl)-6-phenyl-2-pyridyl]oxy}hexanoic acid (m.p.=101° C.)

EXAMPLE 15 ethyl 2-methyl-6-{[4-(4-aminophenyl)-6-phenyl-2-pyridyl]oxy}hexanoate

The procedure in Example 12 is followed but using ethyl 2-methyl-6-{[4-(4-nitrophenyl)-6-phenyl-2-pyridyl] oxy}hexanoate (2.5 g), stannous chloride (5.3 g) and ethanol (100 cc). The residue, after extraction and concentration of the organic phases to dryness, is used as it is in the next stage. (yellow oil)

EXAMPLE 16 ethyl 6-{[4-(4-methylaminophenyl)-6-phenyl-2-pyridyl]oxy}hexanoate

The mixture comprising (3 g) 6-{[4-(4-aminophenyl)-6-phenyl-2-pyridyl] oxy}hexanoate from Example 13, Table XIII, ethyl ortho-formate (5.5 cc) and trifluoroacetic acid 25 drops is refluxed for 17 hours. The reaction mixture is then concentrated to dryness, at 80° C., under reduced pressure (0.13 kPa). The oily residue obtained (3.5 g) is taken up in ethanol (40 cc). To the yellow suspension thus obtained, cooled to 5° C. on an ice bath, is slowly added sodium borohydride (1.1 g). The reaction mixture is then refluxed for 1 hour. The solution obtained is poured in iced water (100 cc), extracted with ethyl ether (100 cc). The combined organic phases are washed with distilled water until neutrality, dried over sodium sulphate and concentrated to dryness at 40° C. under reduced pressure. The oily residue obtained is purified by chromatography under pressure on silica gel (30–60 μmm; eluent: n-hexane-ethyl acetate as a yellow oil)

When the procedure of Example 16 is followed and ethyl 6-{[4-(4-aminophenyl)-6-phenyl-2-pyridyl]oxy}hexanoate is replaced with methyl 6-{[4-(4-aminophenyl)-6-phenyl-2-pyridyl]oxy}-2,2-dimethylhexanoate then the compound prepared is methyl 6-{[4-(4-methylaminophenyl)-6-phenyl-2-pyridyl] oxy}-2,2-dimethylhexanoate. (m.p.=77° C.)

EXAMPLE 17 ethyl 6-{[4-(4-isopropylaminophenyl)-6-phenyl-2-pyridyl]oxy}hexanoate

To a solution of ethyl 6-{[4-(4-aminophenyl)-6-phenyl-2-pyridyl] oxy}hexanoate (3 g) and acetone (0.54 cc) in acetic acid (45 cc), brought to 15° C., is slowly added sodium borohydride (1.14 g) so as to maintain the temperature below 22° C. The mixture is then stirred at room temperature for 4 hours. The reaction mixture is then poured in distilled water (150 cc) and extracted with ethyl ether (2×100 cc). The combined organic phases are washed with distilled water until neutrality, dried over sodium sulphate and concentrated to dryness at 40° C. under reduced pressure. The oily residue obtained is purified by chromatography under pressure on silica gel (30– 60 mm; eluent: n-hexane-ethyl acetate 9-1 as a yellow oil).

EXAMPLE 18

6-{[4-(4-benzamidophenyl)-6-phenyl-2-pyridyl]oxy}hexanoic acid

To a solution of ethyl 6-{[4-(4-aminophenyl)-6-phenyl-2-pyridyl] oxy}hexanoate (4 g), triethylamine (1.7 cc) and a spatula-tip-full of 4dimethylaminopyridine (DMAP) in chloroform (40 cc), is slowly added, at room temperature, benzoyl chloride (1.38 cc) in solution in chloroform (20 cc). The temperature rises up to 33° C. The reaction mixture is then stirred at room temperature for 21 hours and then hydrolysed with distilled water (50 cc). The organic phase is decanted. The aqueous phase is extracted with dichloromethane (2×50 cc). The combined organic phases are washed with distilled water until neutrality, dried over sodium sulphate and concentrated to dryness at 40° C. under reduced pressure. The product is used directly in the next reaction after purification by recrystallization in an n-hexane-ethyl acetate (1-1) mixture (100 cc). The procedure in Example 3 is then followed but using the ethyl 6-{[4-(4-benzamidophenyl)-6-phenyl-2-pyridyl]oxy}hexanoate previously obtained, potassium hydroxide pellets (0.7 g) dissolved in distilled water (15 cc) and ethanol (150 cc). The reaction mixture is refluxed for 2 hours. The product is purified by recrystallization in ethyl acetate (50 cc), whitish crystals (m.p.=167°–169° C.)

EXAMPLE 19

6-{[4-(4-trifluoroacetamidophenyl)-6-phenyl-2-pyridyl]oxy)hexanoic acid

To a solution of 6-{[4-(4-aminophenyl)-6-phenyl-2-pyridyl]oxy}hexanoic acid (1 g) in tetra-hydrofuran (15 cc) is slowly added, at 0° C., trifluoroacetic anhydride (0.5 cc).

The reaction mixture is stirred for 1 hour at room temperature and then poured on ice. The tetrahydrofuran is then evaporated at 25° C. under reduced pressure, the remaining aqueous phase is then extracted with chloroform. The organic phase is washed with distilled water until neutrality and dried over sodium sulphate and then concentrated to dryness at 40° C. under reduced pressure. The solid residue obtained is purified by chromatography under pressure on silica gel (30–60 mm; eluent: n-hexane-ethyl acetate 4-6) and then by two successive recrystallizations, the first in an n-hexane-ethyl acetate (3-5) mixture (40 cc), the second in toluene (20 cc), yellowish crystals; (m.p.=178°–180° C.)

EXAMPLE 20

8-[(4-phenyl-2-quinolyl)oxy]octanoic acid

To a suspension of potassium tert-butylate (26 g) in anhydrous dimethylformamide (800 cc) is added 4-phenyl-2-quinolinone (44.3 g). The mixture is heated 1 hour at 120° C. Ethyl 8-bromooctanoate (50.2 g) is then added in solution in anhydrous dimethyl-formamide (250 cc). The mixture is refluxed for 1 hour, cooled on an ice bath, filtered and concentrated to dryness under reduced pressure. The residue is taken up in water (1 liter). The aqueous phase is acidified to pH 4 with acetic acid and extracted with dichloromethane (3×250 cc). The combined organic phases are washed with distilled water until neutrality, dried over sodium sulphate and concentrated to dryness under reduced pressure. After purification by chromatography under pressure on silica gel (30–60 mm; eluent: n-hexane-ethyl acetate 9-1), the ester thus obtained is treated as in Example 4, but with sodium hydroxide pellets (3 g) dissolved in distilled water (50 cc) and ethanol (500 cc). The product is purified by chromatography under pressure on silica gel (30– 60 mm; n-hexane-ethyl acetate 1-1, white solid; m.p.=68° C.)

EXAMPLE 21

2,2-dimethyl-6-{[4-(4-nitrophenyl)-2-quinolyl]oxy}hexanoic

The mixture comprising methyl 2,2-dimethyl-6-{[4-(4-nitrophenyl)- 2-quinolyl]oxy}hexanoate (2.95 g) and dry lithium iodide (6.1 g) In 2,4,6-collidine (115 cc) is refluxed, under Inert atmosphere, for 1 hour and 30 minutes and then poured in a 2N solution of hydrochloric acid (150 cc) at 0° C. The aqueous phase is extracted with ethyl ether (3×50 cc). The combined organic phases are washed with distilled water until neutrality, dried over sodium sulphate and then concentrated to dryness under reduced pressure. The residue obtained is purified by chromatography on silica gel (30–60 mm; n-hexane-ethyl acetate 1-1, white solid; m.p.=85°–92° C.)

EXAMPLE 22

2,2-dimethyl-6-{[4-(4-methylthiophenyl)-2-quinolyl]oxy}hexanoic acid

The suspension obtained by mixing 4-(4-methylthiophenyl)-2-quinolinone (5 g), methyl 6-bromo-2,2-dimethylhexanoate (6.6 g) and potassium carbonate (2.6 g) in dimethylformamide (50 cc) is heated at 100° C. for 90 hours. The reaction mixture is then poured in distilled water (400 cc). The aqueous phase is filtered and then extracted with ethyl ether (150 cc). The organic phase is washed with distilled water, dried over sodium sulphate and concentrated to dryness under reduced pressure. Excess methyl 6-bromo-2, 2,-dimethylhexanoate is distilled under reduced pressure (bulb distiller; 100° C.— 0.1 mbar). After purification by chromatography on silica gel (50–200 mm; dichloromethane), the ester obtained is treated as in Example 20, but with lithium iodide (4.1 g) and 2,4,6-collidine (80 cc). The reaction mixture is refluxed for 3 hours. The product is purified by chromatography on silica gel (50–200 mm; dichloromethane-methanol 98-2) and recrystallization in a dichloromethane-petroleum ether mixture. (yellowish crystals; m.p.=106°– 107° C.)

EXAMPLE 23

1-[6-(4-phenyl-2-quinolyloxy)hexanoyl]pyrrolidine

To a solution of 5 g of 6-[(4-phenyl-2-quinolyl)oxy] hexanoic acid in 120 cc of tetrahydrofuran is added 2.9 g of 1,1'-carbonyldiimldazole. The mixture is stirred for 2 hours to 50 C. After cooling, 1.3 g of pyrrolidine is added and the mixture is stirred at room temperature overnight. The tetrahydrofuran is removed in vacuo and the residue partitioned between ethyl acetate and water. The ethyl acetate solution is washed with water, dried ($Na_2SO_4$), filtered and concentrated in vacuo. The resultant residue is then purified by flash chromatography on silica gel (30–60mm; eluent: 3:7 cyclohexane/ethyl acetate) to give 1-[6-(4-phenyl-2-quinolyloxy)hexanoyl]pyrrolidine as a white solid (m.p.= 52°–54° C.)

When the procedure of Example 23 is followed and 4-[(4,6 -diphenyl-2-pyridyl)oxy]butanoic acid is used in place of 6-[(4-phenyl-2-quinolyl)oxy] -hexanoic acid and aniline is used in place of pyrrolidine, the the product prepared is 4-[(4,6-diphenyl-2-pyridyl)oxy]-butanilide (m.p.=158° C.)

When the procedure of Example 23 is followed and 4-[(4,6 -diphenyl-2-pyridyl)oxy]butanoic acid is used in place of 6-[(4-phenyl-2-quinolyl)oxy] -hexanoic acid and DBU and glycine ethyl ester hydrochloride are used in place of pyrrolidine, then the product prepared is ethyl N-[4-(4,6 -diphenyl-2-pyridyloxy)-butanoyl]glycinate. (m.p.=93° C.)

EXAMPLE 24

7-(4-phenyl-2-quinolyl)-6-hepten, 1-oic acid

To a suspension of 47.6 g of (6-carboxyhexyl)triphenylphosphonium iodide in 600 cc of toluene is added 21.2 g of potassium ter-butylate. The mixture is heated to 90 C for 2 hours under a nitrogen athmosphere. After cooling, to the resultant orange suspension is added a solution of 10 g of 4-phenyl-2-quinolyl-carboxaldehyde (prepared according to the method of E. A. Fehnel, J.O.C. 1966, 31,2899) in 150 cc of toluene. The mixture is stirred for two hours at room temperature and then poured into 800 cc water and the organic layer discarded. The aqueous layer is acidified to pH 5 with 1N hydrochloric acid and extracted with dichloromethane, (3×200 cc). The combined extracts are washed with water, dried ($Na_2SO_4$) and evaporated in vacuo. The residue is flash chromatographed on silica gel (30– 60mm; eluent: 92:8 n-hexane/ethyl acetate) and recrystallized from 80 cc acetone to give 7-(4-phenyl-2-quinolyl)-6-hepten-1-oic acid as a whitish solid. (m.p.=152°–154° C.)

EXAMPLE 25

7-(4-phenyl-2-quinolyl}heptanoic acid

A mixture of 1.75 g of 7-(4-phenyl-2-quinolyl)-6-hepten-1-oic acid, 0.18 g of palladium on activated carbon (10% w/w) and 100 cc of tetrahydrofuran is hydrogenated under normal pressure for 1 hour at room temperature. After filtration and concentration in vacuo, the solid residue is stirred in 100 cc diethyl ether and then recrystallized from 40 cc acetone to give 7-(4-phenyl-2-quinolyl)eptanoic acid as a whitish solid. (m.p.=137°–139° C.).

When the procedure of example 25 is followed and 7-(3-benzylphenyl)- 6-heptenoic acid is used in place of 7-(4-phenyl-2-quinolyl)-6-hepten- 1-oic acid then the product prepared is 7-(3-benzyl-phenyl)eptanoic acid. (m.p.=39° C.)

EXAMPLE 26 methyl 2,2-dimethyl-6-[(4-phenyl-2-quinolyl)amino]hexanoate

A mixture of 3.2 g of 2-chloro-4-phenyl-quinoline (prepared according to the method of S. Kwon and K. Isagawa, Yoki Gosei Kagaku Shi 1973,31, 313) and 5.9 g of methyl 6-amino-2,2-dimethylhexanoate is heated to 100 C. for 8 hours. After cooling, the residue is purified by chromatography on silica gel (eluent: 98:2 dichloromethane/methanol). to give methyl 2,2-dimethyl- 6-[(4-phenyl-2-quinolyl)amino]hexanoate obtained as an oil.

EXAMPLE 27

2,2-dimethyl-6-[{4-phenyl-2-quinolyl)thio]hexanoic acid methyl 2,2-dimethyl-6-[(4-phenyl-2-quinolyl)thio]hexanoate.

To a solution of 4 g of methyl 2,2-dimethyl-6-mercaptohexanoate in 100 cc of dimethylformamide, is added 0.55 g of sodium hydride (50% w/w dispersion in mineral oil). The mixture is stirred for 2 hours until effervescence has stopped. A solution of 5 g of 2-chloro-4-phenylquinoline in 50 cc of dimethyl-formamide is then added. The obtained mixture is heated to 60 C. for 8 hours. After cooling, 10 cc of methanol is added and the mixture evaporated. The resultant residue is purified by flash chromatography on silica gel (30–60 mm; eluent: 8:2 hexane/ethyl acetate) to give methyl 2,2-dimethyl-6-[(4 -phenyl-2-quinolyl)thio]-hexanoate is obtained as an oil.

When the procedure of example 27 is followed and the compounds of Table XVI below are used in place of 2-chloro-4-phenylquinoline and the compounds of Table XVII below are used in place of methyl 2,2-dimethyl-6-mercaptohexanoate then the corresponding products are prepared. Representative compounds so prepared are identified in Table XVIII below.

Table XVI 2-chloro-4,5-diphenylpyrimidine
2-chloro-7-methoxy-3-phenylquinoline
2-chloro-4-phenylquinazoline
2-chloro-4-phenylquinoline

Table XVII methyl 2,2-dimethyl-8-mercaptooctanoate
ethyl 9-mercaptononanoate
ethyl 6-mercaptohexanoate
ethyl 8-mercaptooctanoate
methyl 8-mercaptooctanoate

Table XVIII 2,2-dimethyl-8-(4,5-diphenyl-2-pyrimidylthio)octanoate (colorless oil)
ethyl 9-(4,5-diphenyl-2-pyrimidylthio)nonanoate (colorless oil)
ethyl 6-(4,5-diphenyl-2-pyrimidylthio)hexanoate (colorless oil)
ethyl 8-(4,5-diphenyl-2-pyrimidylthio)octanoate (colorless oil)
ethyl 8-(7-methoxy-3-phenyl-2-quinolylthio)octanoate (colorless oil)
methyl 8-[(4-phenyl-2-quinolyl)thio]octanoate (oil)

EXAMPLE 28

4-(2-thienyl)-2-quinolinone

To a solution of 2-(2-acetylaminobenzoyl)thiophene (4.8 g) in ethanol (60 cc) is added sodium ethylate (3.2 g). The reaction mixture is refluxed for 9 hours, treated again with sodium ethylate (0.5 g) and then allowed to reflux for 10 hours. The mixture is poured in iced water (200 cc). The precipitate formed is filtered, washed with distilled water until neutrality and then with acetone (3×50 cc) and dried at 40° C. under reduced pressure. The residue thus obtained is recrystallized in ethanol to obtain the product as a yellow solid. (m.p.=262°–264° C.)

EXAMPLE 29

6-(3,5-diphenyl-phenoxy)hexanoic acid

A. 3.5-diphenyl-anisole

To a mixture of 150 cc of tetrahydrofuran and 34 cc of a 3M solution of phenylmagnesium bromide in diethylether at 40° C. under an argon athmosphere, are added 15 g of 3,5-dichloroanisole and 5.5 g of bis(triphenylphosphine)nickel(II) chloride. The resultant black mixture is heated for 6 hours to 65° C. and then poured into 400 cc of a saturated aqueous solution of ammonium chloride. After extraction with ethyl acetate (3×150 cc), the combined organic extracts are washed with water, dried (MgSO₄) and concentrated in vacuo. The resultant residue is flash chromatographed on silica gel (30–60 mm; eluent: 20:0.1 n-hexane/ethyl acetate) and recrystallized from 20 cc of methanol to give 3,5-diphenyl-anisole as a white solid. (m.p.=93°– 94° C.)

B. 3.5-diphenyl-phenol

A mixture of 4.7 g of 3,5-diphenyl-anisole and 5.3 g of pyridinium hydrochloride was heated for 5 hours to 185° C. After cooling, the residue was partitioned between 100 cc of diethyl ether and 120 cc of water. The organic layer wes then washed with water, dried (Na₂SO₄) and evaporated. The resultant residue was suspended in 50 cc of n-hexane and filtered to give 3.75 g (85%) of 3,5-diphenyl-phenol as a white solid. (m.p.=97° C.)

C. ethyl 6-(3.5-diphenyl-phenoxy)hexanoate

To a suspension of 0.78 g of sodium hydride (55 % w/w dispersion in mineral oil) in 300 cc of dimethylformamide was added a solution of 2 g of 3,5-diphenyl-phenol in 10 cc of dimethylformamide, The mixture was stirred for 5 hours at room temperature until effervescence had stopped. 2.2 g of ethyl 6-bromohexanoate was then added and the resultant mixture stirred at room temperature overnight. The mixture was then heated for 20 hours to 40° C. After cooling, the resultant mixture was poured into 100 cc of cold water and extracted with ethyl acetate (3#100 cc). The combined extracts were washed with water, dried ($Na_2SO_4$) and concentrated in vacuo. The resultant residue was flash chromatographed on silica gel (30–60 mm; eluent: 92:8 n-hexane/ethyl acetate) to give 1 g of ethyl 6-(3,5-diphenyl-phenoxy)hexanoate as a oil, used without further purification in the next step.

D. 6-(3,5-diphenyl-phenoxy)hexanoic acid

By using a similar procedure to that described in example 1 but with 1 g of ethyl 6-(3,5-diphenyl-phenoxy)hexanoate, 0.22 g of potassium hydroxide in pellets, 5 cc of water and 5 cc of ethanol as the starting material (2 hours; reflux), and after recrystallization in a mixture of 10 cc of n-hexane and 2 cc of ethyl acetate, 0.5 g (54%) of 6-(3,5-diphenyl-phenoxy)hexanoic acid was obtained as a white solid. (m.p.= 104° C.)

EXAMPLE 30

6-(4-phenyl-2-quinazolinyloxy)hexanoic acid

To a suspension of 1.74 g of potassium 6-hydroxyhexanoate (prepared from e-caprolactone) in 35 cc of sulfolaneat 60° C. was added 0.64 g of sodium hydride (55 % w/w dispersion in mineral oil). The mixture was stirred for 30 minutes to 140° C. until effervescence had stopped. 3 g of 2-chloro-4-phenyl-quinazoline were then added and the resultant mixture was heated for further 2 hours to 140° C. The mixture was poured into 500 cc of water, neutralized with acetic acid and extracted with dichloromethane (3#300 cc). The combined extracts were washed with water, dried ($Na_2SO_4$) and evaporated. The residue was chromatographed on silica gel (50–200 mm; eluent: 95:5 diethyl ether/methanol), then washed with n-hexane and filtered to give 0.4 g (10%) of 6-(4-phenyl-2-quinazolinyloxy)hexanoic acid as a whitish solid. (m.p.=112°–114° C.)

EXAMPLE 31

7-(3-benzyl-phenyl)6-heptenoic acid

By using a similar procedure to that described in example 24 but with 1 g of 3-benzylbenzaldehyde, 5.5 g of (6-carboxyhexyl)triphenylphosphonium iodide, 2.5 g of potassium ter-butylate and 40 cc of toluene as the starting material (1 hour; 50° C.), and after purification by flash chromatography on silica gel (30–60 Mm; eluent: 8:2:0.05 n-hexane/ethyl acetate/acetic acid), 7-(3-benzyl-phenyl)-6-heptenoic acid is obtained. (m.p.=68° C.)

The starting 3-benzyl-benzaldehyde is prepared in an analogous manner that is described for 3,5-diphenyl-anisole in example 29 but with 23 g of 2-(3-bromophenyl)-1,3-dioxolan in place of 3,5-dichloroanisole, 62 cc of a 3M solution of benzylmagnesium bromide in terahydrofuran in place of a 3M solution of phenylmagnesium bromide in diethylether, 0.87 g of bis(triphenylphosphine)-nickel(11) chloride and 200 cc of tetrahydrofuran as the starting material, followed by a deprotection step with a mixture of 46 g of silica gel (50–200 mm), 4.6 cc of a 10% aqeous solution of oxalic acid in 250 cc of dichlorometahne, results in 3-benzyl-benzaldehyde. (whitish solid-oil).

EXAMPLE 32 methyl 2,2-dimethyl-6-[(4,6-diphenyl-2-pyridyl)oxy]hexanoate

The procedure In Example 4 is followed but using 4,6-diphenyl-2-pyridinone (4 g), methyl 6-bromo-2,2-dimethylhexanoate (5.8 g) (prepared according to the method described in Patent EP 108 592), silver carbonate (2.3 g) and toluene (150 cc). The product is purified by chromatography under pressure on silica gel (30–60 mm; eluent: n-hexane-ethyl acetate 95-5, brown oil)

EXAMPLE 33

2,2-dimethyl-6-[(4,6-diphenyl-2-pyridyl)oxy]hexanoic acid.

The procedure in Example 6 is followed but using methyl 2,2-dimethyl-6-[(4,6-diphenyl-2-pyridyl) oxy]hexanoate (5 g), potassium hydroxide pellets (1.1 g) and ethanol (100 cc). The reaction mixture is refluxed for 24 hours. The product is purified by chromatography under pressure on silica gel (30–60 mm; eluent: n-hexane-ethyl acetate 8-2), white crystals (m.p.=115° C.)

EXAMPLE 34 methyl 2-ethyl-6-[(4,6-diphenyl-2-pyridyl)oxy]hexanoate

The procedure in Example 5 is followed but using 4,6-diphenyl-2-pyridinone (2.8 g) (prepared by analogy with the method described in Patent EP 108 592 from methyl butanoate), methyl 6-bromo-2-ethylhexanoate (5.4. g), silver carbonate (1.6 g) and dimethylformamide (100 cc). The reaction mixture is heated at 100° C. for 31 hours then at 120° C. for 40 hours. The product is purified by chromatography under pressure on silica gel (30–60 mm; eluent: n-hexane-ethyl acetate 9-1). (yellow oil)

EXAMPLE 35

2-ethyl-6-[(4,6-diphenyl-2-pyridyl)oxy]hexanoic acid.

The procedure in Example 6 is followed but using methyl 2-ethyl-6-[(4,6-diphenyl-2-pyridyl)oxy]hexanoate (3.15 g), potassium hydroxide pellets (0.9 g) dissolved in distilled water (20 cc) and ethanol (100 cc). The reaction mixture is refluxed for 8 hours. The product is purified by recrystallisation in an n-hexane-ethyl acetate (2-1) mixture (40 cc), white crystals (m.p.=115° C.)

EXAMPLE 36 ethyl 2-ethyl-2-methyl-6-[(4,6-diphenyl-2-pyridyl)oxy]hexanoate,

The procedure in Example 5 is followed but using 4,6-diphenyl-2-pyridinone (3 g), ethyl 6-bromo-2-ethyl-2-methylhexanoate (6.44 g) [prepared according to the method of K. E. MOELLER, Brenstoff-Chem., 47, 10 (1966)], silver carbonate (1.68 g) and dimethylformamide (110 cc). The reaction mixture is heated at 100° C. for 121 hours. The product is purified by chromatography under pressure on silica gel (30–60 mm; eluent: n-hexane-ethyl acetate 9- 1). (yellow oil)

EXAMPLE 37

2-ethyl-2-methyl-6-[(4,6-diphenyl-2-pyridyl)oxy]hexanoic acid

The procedure in Example 6 is followed but using ethyl 2-ethyl-2 -methyl-6-[(4,6-diphenyl-2-pyridyl)oxy]hexanoate (3.6 g), potassium hydroxide pellets (0.95 g) dissolved in distilled water (20 cc) and ethanol (50 cc). The reaction mixture is refluxed for 120 hours. The product is purified by chromatography under pressure on silica gel (30–60 mm; eluent: n-hexane-ethyl acetate 75-25) and then by recrystaliisation in an n-hexane-ethyl acetate (2-1) mixture (40 cc), white crystals (m.p.=119°–120° C.)

EXAMPLE 38 ethyl 2-methyl-6-{[4-(3,4-methylenedioxyphenyl)-6-phenyl-2-pyridyl]oxy} hexanoate The procedure in Example 5 is followed but using 4-(3,4-methylenedioxyphenyl)-6-phenyl-2-pyridinone (2.5 g), ethyl 6-bromo-2-methylhexanoate (4 g), silver carbonate (1.2 g) and dimethylformamide (100 cc). The reaction mixture is heated at 100° C. for 72 hours. The product is purified by chromatography under pressure on silica gel (30–60 mm; eluent: n-hexane-ethyl acetate 9-1). (yellowish oil)

EXAMPLE 39

2-methyl-6-{[4-(3,4-methylenedioxyphenyl)-6-phenyl-2-pyridyl]oxy=acid

The procedure in Example 6 is followed but using ethyl 2-methyl- 6-{[4-(3,4-methylenedioxyphenyl)-6-phenyl-2-pyridyl]oxy}hexanoate (2.6 g), potassium hydroxide pellets (0.5 g) dissolved in distilled water (10 cc) and ethanol (150 cc). The reaction mixture is refluxed for 4 hours. The product is purified by recrystallisation in an n-hexane-ethyl acetate (5-3) mixture (80 cc).white crystals. (m.p.= 123°–125° C.)

EXAMPLE 40

2,2-dimethyl-6-[(4,6-diphenyl-2-pyridyl)oxy]hexanonitrile

The procedure in Example 4 is followed but using 4,6-diphenyl-2-pyridinone (6.3 g)0 6-bromo-2,2-dimethylhexanonitrile (2.60 g) (prepared according to the method of M. Larchevêque et al., Bull. Soc. Chim. Fr., 1710 (1974)), silver carbonate (3.5 g) and toluene (300 cc). The product is purified by chromatography under pressure on silica gel (30–60 mm); eluent: n-hexane-ethyl acetate 9.5-0.5).yellowish solid. (m.p.=71° C.)

EXAMPLE 41

5-{1,1-dimethyl-5-[(4,6-diphenyl-2-pyridyl)oxy]pentyl}-[1H]-tetrazole

The procedure in Example 9 is followed but using 2,2-dimethyl-6-[ (4,6-diphenyl-2-pyridyl)oxy]hexanonitrile (3.5 g), sodium nitride (2.4 g), ammonium chloride (2 g) and dimethyl formamide (40 cc). The reaction mixture is heated at 120° C. for 96 hours. The product is purified by chromatography under pressure on silica gel (30–60 mm; eluent: n-hexane-ethyl acetate 9-1). The solid residue obtained is taken up in ethyl ether (100 cc). After stirring for 1 hour at room temperature, the solid is separated by filtration, washed with ethyl ether (3 30 cc) and then dried under reduced pressure, white solid. (m.p.=160°–162° C.)

EXAMPLE 42

In some cases, various stereoisomeric products may exist. This invention is not limited to any particular stereoisomer but includes all possible individual isomers and mixtures thereof. The stereoisomers of the compounds of this invention can be separated according to standard methods known in the art, for example directly by chromatography on chiral support or by separation of pure diastereoisomeric precursors. For example, the N-[6-(4,6-diphenyl-2 -pyridyloxy)-2-methylhexanoyl]-(1R,5S)-10,2-camphorsultam can be obtained by adding dropwise a solution of 1.8 g of 6-(4,6-diphenyl-2-pyridyloxy)-2-methylhexanoyl chloride in 10 cc of toluene to a mixture of 2 g of (+)-10,2-camphorsultam and 0.44 g of sodium hydride (50% w/w dispersion in mineral oil) in 20 cc of toluene. The obtained mixture is stirred overnight. After adding 70 cc of water, the mixture is extracted with toluene (3×70 cc). The combined extracts are dried over magnesium sulfate, filtered and evaporated to give 0.7 g of the expected diastreoisomeric mixture (50/50). The diastereisomers can be separated by high liquid pressure chromatography on chiral support CHIRACEL OD; 1 ml/mn; P=49 bars; eluent: 95:5 heptane/ethanol; retention times: 9.84 and 12.01 mn respectively). The pure stereoisomeric 6-(4,6 -diphenyl-2-pyridyloxy)-2-methyl-hexanoic acids can be prepared from the pure previously described diastereoisomers by saponification, according to the method of W. (ppolzer et al., Tetrahedron Letters, 1989, 30, 5603 and 6009.

Compounds within the scope of the present invention have potent activity as leukotriene $B_4$ antagonists and as such possess therapeutic value in the treatment of Inflammatory conditions and hypersensitivity responses. $LTB_4$ is implicated in diseases such as rheumatoid arthritis, gout, psoriasis and inflammatory bowel disease and therefore compounds which demonstrate $LTB_4$ antagonist properties are useful in the control of these disease states. Compounds of general formula I and their salts are also particularly useful in the osteoarticulatory field. By virtue of their affinity for leukotriene $B_4$ receptors, they interfere with this agonist by blocking its action at the receptor level.

Their affinity for leukotriene $B_4$ receptors has been successfully demonstrated by measuring their effect on the binding to tritium-labelled leukotriene $B_4$ using guinea-pig spleen membranes, according to a method inspired by the method of J. B. Cheng, J. of Pharmacology and Experimental Therapeutics, 236, 126 (1986). In this technique, compounds according to the invention are active at concentrations of between about 0.5 to about 5,000 nM ($IC_{50}$). Further, compounds of this invention are shown to be leukotriene $B_4$ antagonists in the technique of guinea-pig pulmonary parenchyma contraction antagonism induced by $LTB_4$ described by P. Sirois et al., Pharmacology, 31, 225–236 (1985). In this technique, products are active at concentrations of between about 1 to about 10,000 nM. When compounds of this invention are used in these tests it can be shown that they are considered to be active as leukotriene $B_4$ antagonists. The results of representative compounds so tested are shown below in Table XIX.

TABLE XIX

| Compound | IC$_{50}$/nM Binding (Cheng) | L. Parenchyma |
|---|---|---|
| 6-[(4,6-diphenyl-2-pyridyl)oxy]hexanoic acid | 3 | 300 |
| 2,2-dimethyl-6-[(4,6-diphenyl-2-pyridyl)oxy]-hexanoic acid | 5 | 10 |
| 7-[(4,6-diphenyl-2-pyridyl)oxy]heptanoic acid | 25 | 1300 |
| 5-[(4,6-diphenyl-2-pyridyl)oxy]pentanoic acid | 50 | 2000 |
| 4-[(4,6-diphenyl-2-pyridyl)oxy]butanoic acid | 300 | |
| 2,2-dimethyl-7-[(4,6-diphenyl-2-pyridyl)oxy]heptanoic acid | 15 | 30 |
| 2-methyl-6-[(4,6-diphenyl-2-pyridyl)oxy]hexanoic acid | 4 | 10 |
| 2-ethyl-6-[(4,6-diphenyl-2-pyridyl)oxy]hexanoic acid | 3 | 70 |
| 2-ethyl-2-methyl-6-[(4,6-diphenyl-2-pyridyl)oxy]hexanoic acid | 17 | 30 |
| 2,2-dimethyl-8-[(4,6-diphenyl-2-pyridyl)oxy]octanoic acid | 22 | |
| methyl 6-[(4,6-diphenyl-2-pyridyl)oxy]hexanoate | 40 | >10000 |
| 6-{[4-(4-chlorophenyl)-6-phenyl-2-pyridyl]oxy}hexanoic acid | 10 | 1000 |
| 2,2-dimethyl-6-{[4-(4-chlorophenyl)-6-phenyl-2-pyridyl]oxy}hexanoic acid | 100 | |
| ethyl 6-{[6-(4-chlorophenyl)-4-phenyl-2-pyridyl]oxy}hexanoate | 5000 | |
| 6-{[6-(4-chlorophenyl)-4-phenyl-2-pyridyl]oxy}hexanoic acid | 1000 | |
| 6-{[4-(4-methoxyphenyl)-6-phenyl-2-pyridyl]oxy}hexanoic acid | 15 | 1100 |
| 2,2-dimethyl-6-{[4-(4-methoxyphenyl)-6-phenyl-2-pyridyl]oxy}hexanoic acid | 50 | 170 |
| 2-methyl-6-{[4-(4-methoxyphenyl)-6-phenyl-2-pyridyl]oxy}hexanoic acid | 4 | 20 |
| 6-{[6-(4-methoxyphenyl)-4-phenyl-2-pyridyl]oxy}hexanoic acid | 1000 | |
| 6-{[6-(4-trifluoromethylphenyl)-4-phenyl-2-pyridyl]oxy}hexanoic acid | 1200 | |
| 6-{[4,6-di(4-chlorophenyl)-2-pyridyl]oxy}hexanoic acid | 1200 | |
| 6-{[6-(4-methylphenyl)-4-phenyl-2-pyridyl]oxy}hexanoic acid | 300 | |
| 6-{[6-(4-chlorophenyl)-4-(4-methoxyphenyl)-2-pyridyl]oxy}hexanoic acid | 1200 | >10000 |
| 6-{[4-(4-chlorophenyl)-6-(4-methoxyphenyl)-2-pyridyl]oxy}hexanoic acid | 1700 | |
| 6-{[4-(2-fluorophenyl)-6-phenyl-2-pyridyl]oxy}hexanoic acid | 10 | 1700 |
| 6-{[6-phenyl-4-(4-trifluoromethylphenyl)-2-pyridyl]oxy}hexanoic acid | 110 | |
| 6-{[4-(3-methoxyphenyl)-6-phenyl-2-pyridyl]oxy}hexanoic acid | 8 | 200 |
| 2,2-dimethyl-6-{[4-(3-Methoxyphenyl)-6-phenyl-2-pyridyl]oxy}hexanoic acid | 2 | 30 |
| 6-{[4,6-di(4-methoxyphenyl)-2-pyridyl]oxy}hexanoic acid | 3000 | |
| 6-{[4-(4-fluorophenyl)-6-phenyl-2-pyridyl]oxy}hexanoic acid | 3 | 800 |
| 2,2-dimethyl-6-{[4-(4-fluorophenyl)-6-phenyl-2-pyridyl]oxy}hexanoic acid. | 7 | 300 |
| 6-{[6-(4-fluorophenyl)-4-phenyl-2-pyridyl]oxy}hexanoic acid | 30 | 1700 |
| 6-{[6-(fluorophenyl)-4-phenyl-2-pyridyl]oxy}hexanoic acid | 3 | 60 |
| 6-{[6-(3-methoxyphenyl)-4-phenyl-2-pyridyl]oxy}hexanoic acid | 500 | |
| 6-{[4-(3,4-dichlorophenyl)-6-phenyl-2-pyridyl]oxy}hexanoic acid | 500 | |
| 6-{[4-(4-methylphenyl)-6-phenyl-2-pyridyl]oxy}hexanoic acid | 15 | 100 |
| 6-{[4-(3-chlorophenyl)-6-phenyl-2-pyridyl]oxy}hexanoic acid | 4 | |
| sodium 6-{[6-(2-chlorophenyl)-4-phenyl-2-pyridyl]oxy}hexanoate | 1.8 | 200 |
| 6-{[4-(2-chlorophenyl)-6-phenyl-2-pyridyl]oxy}hexanoic acid | 200 | |
| 2-methyl-6-{[4-(3-chlorophenyl)-6-phenyl-2-pyridyl]oxy}hexanoic acid | 5.5 | 1000 |
| 2-methyl-6-{[4-(4-chlorophenyl)-6-phenyl-2-pyridyl]oxy}hexanoic acid | 5.5 | 70 |
| 2,2-dimethyl-6-{[4-(3-chlorophenyl)-6-phenyl-2-pyridyl]oxy}hexanoic acid | 13 | 1000 |
| 2-methyl-6-{[6-(2-fluorophenyl)-4-phenyl-2-pyridyl]oxy}hexanoic acid | 4 | 6 |
| 2,2-dimethyl-6-{[6-(2-fluorophenyl)-4-phenyl-2-pyridyl]oxy}hexanoic acid | 5 | 80 |
| 6-{[6-(3-fluorophenyl)-4-phenyl-2-pyridyl]oxy}hexanoic acid | 4 | 150 |
| 6-{[4-[3-fluorophenyl)-6-phenyl-2-pyridyl]oxy}hexanoic acid | 3 | 200 |
| 2-methyl-6-{[4-(4-fluorophenyl)-6-phenyl-2-pyridyl]oxy}hexanoic acid | 1.7 | 60 |
| 6-{[4-(4-fluorophenyl)-6-(2-fluorophenyl)-2-pyridyl]oxy}hexanoic acid | 10 | 1000 |
| 2-methyl-6-{[4-(3-methoxyphenyl)-6-phenyl-2-pyridyl]oxy}hexanoic acid. | 5 | 20 |
| 6-{[4-(4-methylthiophenyl)-6-phenyl-2-pyridyl]oxy}hexanoic acid | 10 | 3000 |
| 6-{[4-(3,4-methylenedioxyphenyl)-6-phenyl-2-pyridyl]oxy}hexanoic acid | 1 | 5 |
| 2-methyl-6-{(4-(3,4-methylenedioxyphenyl)-6-phenyl-2-pyridyl]oxy}-hexanoic acid | 7 | 2.5 |
| 2,2-dimethyl-6-{[4-(3,4-methylenedioxyphenyl)-6-phenyl-2-pyridyl]oxy}-hexanoic acid | 7 | 140 |
| 6-{[4-(3-methylphenyl)-6-phenyl-2-pyridyl]oxy}hexanoic acid | 15 | |
| 2-methyl-6-{[4-(4-methylphenyl)-6-phenyl-2-pyridyl]oxy}hexanoic acid | 13 | 20 |
| 6-{[4-(4-dimethylaminophenyl)-6-phenyl-2-pyridyl]oxy}hexanoic acid | 30 | 6000 |
| 6-{[4-(4-nitrophenyl)-6-phenyl-2-pyridyl]oxy}hexanoic acid | 50 | |
| 6-{[4-phenyl-6-(2-thienyl)-2-pyridyl]oxy}hexanoic acid | 50 | 300 |
| 2,2-dimethyl-6-{[4-phenyl-6-(2-thienyl)-2-pyridyl]oxy}hexanoic acid | 15 | 1000 |
| 6-{[4-phenyl-6-(3-thienyl)-2-pyridyl]oxy}hexanoic acid | 10 | 1000 |
| 2,2-dimethyl-6-{[4-phenyl-6-(3-thienyl)-2-pyridyl]oxy}hexanoic acid | 5 | 100 |
| 6-[(4-phenyl-2-quinolyl)oxy]hexanoic acid | 700 | |
| 2-methyl-6-[(4-phenyl-2-quinolyl)oxy]hexanoic acid | 550 | |
| 2,2-dimethyl-6-[(4-phenyl-2-quinolyl)oxy]hexanoic acid | 150 | |
| 2-ethyl-2-methyl-6-[(4-phenyl-2-quinolyl)oxy]hexanoic acid | 110 | |
| 7-[(4-phenyl-2-quinolyl)oxy]heptanoic acid | 1800 | |
| 8-[(4-phenyl-2-quinolyl)oxy]octanoic acid | 2000 | |
| 6-{[4-(4-chlorophenyl)-2-quinolyl]oxy}hexanoic acid | 30 | |
| 2-methyl-6-{[4-(4-chlorophenyl)-2-quinolyl]oxy}hexanoic acid | 30 | |
| 2-ethyl-6-{[4-(4-chlorophenyl)-2-quinolyl]oxy}hexanoic acid | 200 | |
| 2,2-dimethyl-6-{[4-(4-chlorophenyl)-2-quinolyl]oxy}hexanoic acid | 15 | |
| 2,2-dimethyl-6-{[4-(3-chlorophenyl)-2-quinolyl]oxy}hexanoic acid | 1100 | |
| 2,2-dimethyl-6-{[4-(2-fluorophenyl)-2-quinolyl]oxy}hexanoic acid | 800 | |
| 2,2-dimethyl-6-{[4-(4-fluorophenyl)-2-quinolyl]oxy}hexanoic acid | 150 | |
| 2,2-dimethyl-6-{[4-(3,4-dichlorophenyl)-2-quinolyl]oxy}hexanoic acid | 3500 | |
| 2,2-dimethyl-6-[(6-chloro-4-phenyl-2- | 2500 | |

TABLE XIX-continued

| quinolyl)oxy}hexanoic acid | | |
|---|---|---|
| 2,2-dimethyl-6-[(7-chloro-4-phenyl-2-quinolyl)oxy}hexanoic acid | 2000 | |
| 2,2-dimethyl-6-{[4-(4-nitrophenyl)-2-quinolyl]oxy}hexanoic acid | 150 | |
| 2,2-dimethyl-6-{[4-(3-methoxyphenyl)-2-quinolyl]oxy}hexanoic acid | 300 | |
| 2,2-dimethyl-6-{[4-(4-methoxyphenyl)-2-quinolyl]oxy}hexanoic acid | 10 | |
| 2-methyl-6-{[4-(4-methoxyphenyl)-2-quinolyl]oxy}hexanoic acid | 16 | |
| 2,2-dimethyl-6-{[4-(3-tolyl)-2-quinolyl]oxy}hexanoic acid | 3500 | |
| 2,2-dimethyl-6-{[4-(4-tolyl)-2-quinolyl]oxy}hexanoic acid | 30 | |
| 2,2-dimethyl-6-[(7-methyl-4-phenyl-2-quinolyl)oxy}hexanoic acid | 2000 | |
| 2,2-dimethyl-6-{[4-(4-trifluoromethyl-phenyl)-2-quinolyl]oxy}hexanoic acid | 300 | |
| 2,2-dimethyl-6-{[4-(4-dimethylamino-phenyl)-2-quinolyl]oxy}hexanoic acid | 30 | |
| 2,2-dimethyl-6-{[4-(2-thienyl)-2-quinolyl]oxy}hexanoic acid | 200 | |
| 6-[(4,6-diphenyl-2-pyridyl)oxy]-hexanamide | 160 | >10000 |
| 5-{[5-(4,6-diphenyl-2-pyridyl)oxy]-pentyl}[1H]-tetrazole | 10 | 10 |
| 5-{1,1-dimethyl-5-(4,6-diphenyl-2-pyridyl)oxy]pentyl}[1H]-tetrazole | 7 | 20 |
| 5-{5-[(4-phenyl-2-quinolyl)oxy]pentyl}-[1H]-tetrazole | 500 | |
| 5-{1,1-dimethyl-5-[(4-phenyl-2-quinolyl)-oxy]pentyl}[1H]-tetrazole | 400 | |
| 5-{1,1-dimethyl-5-{[4-(4-chlorophenyl)-2-quinolyl]oxy}pentyl-[1H]-tetrazole | 30 | |
| 5-{5-{[4-(4-chlorophenyl)-2-quinolyl]-oxy}pentyl}[1H]-tetrazole | 25 | |
| Sodium 2-{3-[(4,6-diphenyl-2-pyridyl)-oxy]propyloxy}acetate | 100 | |
| 6-{[4-(4-aminophenyl)-6-phenyl-2-pyridyl]oxy}hexanoic acid | 2 | 40 |
| 2-methyl-6-{[4-(4-aminophenyl)-6-phenyl-2-pyridyl]oxy}hexanoic acid | 5 | 20 |
| 2,2-dimethyl-6-{[4-(4-aminophenyl)-6-phenyl-2-pyridyl]oxy}hexanoic acid | 10 | 1 |
| 6-{[4-(3-aminophenyl)-6-phenyl-2-pyridyl]oxy}hexanoic acid | 12 | |
| 2,2-dimethyl-6-{[4-(4-aminophenyl)-2-quinolyl]oxy}hexanoic acid | 40 | |
| 6-{[4-(4-methylaminophenyl)-6-phenyl-2-pyridyl]oxy}hexanoic acid | 5 | 150 |
| 6-{[4-(4-isopropylaminophenyl)-6-phenyl-2-pyridyl]oxy}hexanoic acid | 22 | |
| 6-{[4-(4-benzamidophenyl)-6-phenyl-2-pyridyl]oxy}hexanoic acid | 4000 | |
| 6-{[4-(4-trifluoroacetamidophenyl)-6-phenyl-2-pyridyl]oxy}hexanoic acid | 150 | |
| 6-{[4-(4-methylaminophenyl)-6-phenyl-2-pyridyl]oxy}2,2-dimethyl-hexanoic acid | 8 | |
| 6-{[6-(2-chlorophenyl)-4-(3,4-methylene-dioxyphenyl)-2-pyridyl]oxy}2-methyl-hexanoic acid | 2 | |
| 5-{5-{[6-phenyl-4-(3,4-methylenedioxy-phenyl)-2-pyridyl]oxy}pentyl}1H-tetrazole | 2 | |
| 2,2-dimethyl-6-[(3-methyl-4-phenyl-2-quinolyl)oxy]hexanoic acid | 8000 | |
| 6-[(4-phenyl-2-pyridyl)oxy]hexanoic acid | 900 | |
| 6-[(4-phenyl-2-pyridyl)oxy]2,2-dimethylhexanoic acid | 40 | 3000 |
| 6-{[4-(4-chlorophenyl)-2-pyridyl]oxy}-2,2-dimethylhexanoic acid | 20 | |
| 6-[(6-ter-butyl-4-phenyl-2-pyridyl)oxy]-hexanoic acid | 300 | 2000 |
| 6-[(6-ter-butyl-4-phenyl-2-pyridyl)oxy]-2,2-dimethylhexanoic acid | 40 | 1000 |
| 6-[(6-methyl-4-phenyl-2-pyridyl)oxy]-hexanoic acid | 200 | |
| 6-[(6-methyl-4-phenyl-2-pyridyl)oxy]-2,2-dimethylhexanoic acid | 10 | |
| 6-[(6-cyclopropyl-4-phenyl-2-pyridyl)-oxy]hexanoic acid | 40 | |
| 6-[(6-cyclopropyl-4-phenyl-2-pyridyl)-oxy]2,2-dimethylhexanoic acid | 4 | 200 |
| 6-[(6-methyl-4-phenyl-2-quinolyl)oxy]-2,2-dimethylhexanoic acid | 5000 | |
| 4-[(4,6-diphenyl-2-pyridyl)oxy]butanilide | >1000 | |
| 4-[(4,6-diphenyl-2-pyridyl)oxymethyl]-benzoic acid | 350 | 10000 |
| N-[4-(4,6-diphenyl-2-pyridyloxy)-butanoyl]glycine | 16 | |
| 6-[(4,6-diphenyl-2-pyrimidyl)oxy]-hexanoic acid | 150 | |
| 6-[(4,6-diphenyl-2-pyrimidyl)oxy]2,2-dimethylhexanoic acid | 10 | 1000 |
| 6-[(5,6-diphenyl-2-pyridyl)oxy]2,2-dimethylhexanoic acid | 10000 | |
| sodium 8-[(5,6-diphenyl-2-pyridyl)oxy]-octanote | 10000 | |
| 8-{[5,6-bis-(4-methoxyphenyl)-2-pyridyl]oxy}octanoic acid | 3000 | |
| 6-[(6-phenyl-2-pyridyl)oxy]2,2-dimethylhexanoic acid | 2000 | |
| sodium 8-[(6-phenyl-2-pyridyl)oxy]-octanate | 6000 | |
| 2,2-dimethyl-8-(4,5-diphenyl-2-pyrimidylthio)octanoic acid | 2500 | |
| 8-(4,5-diphenyl-2-pyrimidyloxy)octanoic acid | 8500 | |
| 6-[4,5-bis-(4-methoxyphenyl)-2-pyrimidyloxy]hexanoic acid | 8000 | |
| 6-(4,5-diphenyl-2-pyrimidylthio)hexanoic acid | 8000 | |
| sodium 8-(4,5-diphenyl-2-pyrimidylthio)-octanoate | 3000 | |
| 6-(3,5-diphenyl-phenoxy)hexanoic acid | 8 | |
| 7-(3-benzyl-phenyl)6-heptenoic acid | 10000 | |
| 7-(3-benzylphenyl)heptanoic acid | 7000 | |
| sodium 8-(4-phenyl-2-quinazolylthio)-octanoate | 9000 | |

| Compound | Binding (Cheng) % Inhibition at 10 μM |
|---|---|
| 1-[6-(phenyl-2-quinolyloxy)hexanoyl]-pyrrolidine | 12 |
| 7-(4-phenyl-2-quinolyl)-6-hepten-1-oic acid | 27 |
| 7-(4-phenyl-2-quinolyl)heptanoic acid | 36 |
| 2,2-dimethyl-6-[(4-phenyl-2-quinolyl)thio]-hexanoic acid | 33 |
| 6-{[4-(2-methoxyphenyl)-2-quinolyl]oxy}-2,2-dimethylhexanoic acid | 36 |
| 6-[(6-methoxy-4-phenyl-2-quinolyl)oxy]-hexanoic acid | 30 |
| sodium 8-[(4-phenyl-2-quinolyl)thio]-octanoate | 31 |
| 6-{[6-phenyl-4-(3,4-dimethoxyphenyl)-2-pyridyl]oxy}hexanoic acid | 21 |
| 6-{[6-phenyl-4-(4-carboxyphenyl)-2-pyridyl]oxy}hexanoic acid | 32 |
| 6-{[6-phenyl-4-(3,5-dimethoxyphenyl)-2-pyridyl]oxy}hexanoic acid | 50 |
| 6-[(5,6-diphenyl-2-pyridyl)oxy]hexanoic acid | 15 |
| 6-{[5,6-bis-(4-methoxyphenyl)-2-pyridyl]-oxy}hexanoic acid | 37 |
| 6-[4,5-bis-(4-chlorophenyl)-2-pyrimidyl-oxy]hexanoic acid | 48 |
| 7-(4,5-diphenyl-2-pyrimidyloxy)heptanoic acid | 22 |
| 6-(4,5-diphenyl-2-pyrimidyloxy)hexanoic acid | 35 |

Furthermore, compounds within the scope of this invention have the advantage of being of very low toxicity. As demonstrated in mice, toxicity is generally greater than 200 mg/kg by the oral route.

Further tests can be used to determine the effectiveness of compounds of this invention such as the following. The $LTB_4$ guinea pig polymorphonuclear membrane binding assay can be used to determine compounds exhibiting $LTB_4$ receptor binding properties. Compounds active in this assay can then be subjected to the guinea pig peritoneal PMN $LTB_4$-induced aggregation assay. THE $LTB_4$-induced aggregation assay determines the antagonistic activity of a compound. The guinea pig $LTB_4$-induced wheal assay is used to determine in vivo activity.

Assay for Inhibitors of ($^3$H)-$LTB_4$ Binding to Membranes From Guinea Pig Polymorphonuclear Leukocytes Preparation of Test Compounds Dissolve compounds to a concentration 100-fold higher than the highest desired concentration for testing. Serially dilute the compound so that all dilutions are 100-fold higher than the assay concentration desired. Compounds are typically dissolved in DMSO. If compounds are insoluble in DMSO, solutions are heated or sonicated to induce solubilization. Compounds may also be dissolved in ethanol.

Final assay concentrations of DMSO and ethanol can be as high as 1.0% and 2.0% (v/v); these concentrations have no measurable effects on specific binding.

Preparation of the Membrane Receptor Fraction

To obtain polymorphonuclear leukocytes (PMNs), 25–30 male Hartley guinea pigs (250–350 g) are intraperitoneally injected with 6 mls of an 8% sodium caseinate solution. 18 to 24 hours later, the guinea pigs are sacrificed by decapitation. The peritoneal cavity is lavaged with 15 mls of isolation buffer. The cells are collected and centrifuged at 200×g for 10 minutes. Contaminating red blood cells can be removed by hypotonic lysis. The cells are resuspended in isolation buffer and centrifuged as before. They are filtered through gauze and centrifuged again. The resulting pellet is suspended in 3 ml of sonication buffer, counted and brought to a concentration of 1 x 108 cells/ml. This suspension is lysed on ice with 5 bursts of 30 seconds separated by 1 minute intervals. The homogenate is centrifuged at 200×g for 10 minutes at 4° C. Aliquots of supernatant are transferred to high speed centrifuge tubes (1 tube per 3 guinea pigs). The tubes are centrifuged at 49,000×g for 15 minutes at 4° C. The pellets are resuspended by three 5 second bursts of sonication, separated by 20 second intervals. This suspension is centrifuged at 50,000×g for 20 minutes at 4° C. Pellets are stored at −70° C. for up to 3 months.

To use in the binding assay, the pellet is thawed at room temperature and suspended in 9 mls of assay buffer (sonication may be necessary).

Binding Assay

Each assay tube (16×100 mm) contains the following:
345 ml Assay Buffer
5 ml Test compound or solvent
50 ml 3H-$LTB_4$ (0.50 nM)
100 ml Protein preparation (0.2 mg)

Incubations are done at 30° C. for 40 minutes in a water bath. Reactions are stared by the addition of ($^3$H)-$LTB_4$ solution. Samples are collected via a Brandel M24 Harvester for binding assays. Tubes should be washed with a total of 19 ml cold wash buffer.

The filters are transferred to 7 ml plastic scintillation vials to which 6.0 ml of appropriate scintillation fluid (e.g., Scintiverse®) is added. After being allowed to equilibrate for 12 hours, the radioactivity is counted with a liquid scintillation counter appropriately set for tritium.

The required control assay tubes include the following:

(a) Total Binding: No test compound is added; buffer is substituted.

(b) Non-Specific Binding: Non-labeled ligand is added at a concentration of 1 mM.

(c) Solvent Controls: If test compound is dissolved in a solvent, controls for both Total Binding and Non-Specific Binding containing solvent but no compounds are required.

Calculations

Specific binding is defined as that amount of radioligand prevented from binding by 1000-fold excess non-labeled ligand, i.e., total binding minus non-specific binding. This operational definition is verified by Scatchard analysis of total binding.

Inhibition of specific binding is defined as the decrease in specific binding caused by the test compound, $$\frac{SB_C - SB_T}{SB_C} \times 100$$

where $SB_C$ is the specific binding in the absence of test compound and SBT is the specific binding in the presence of test compound. The $I_{50}$ values (concentrations required to inhibit specific binding by 50%) are determined by graphic analysis of the specific binding observed in the presence of various concentrations of test compound.

The results of this test indicate that compounds of this invention exhibit valuable $LTB_4$ receptor binding properties which are useful in the treatment of inflammatory conditions and hypersensitivity responses.

$LTB_4$-Induced Wheal Formation in Guinea Pig $LTB_4$ plays the role of a mediator in cellular induced inflammation. The induction of chemokinesis and chemotaxis of PMNs and macrophage by $LTB_4$ have contributed to its association with the vascular aspects of acute inflammatory reactions.

In this test intradermal injection of 0.1 ml of a 10 mg/ml solution of $LTB_4$ to guinea pig back skin causes the formation of a wheal. This wheal is visualized by the prior intravenous injection with the indicator 1% Evan's Blue dye. Following a 2 hour incubation post-$LTB_4$ challenge, the guinea pigs are euthanized via $CO_2$ asphyxiation. Their dorsal skins are reflected and the diameters of the challenged sites are compared with those of the vehicle control injected sites.

Preparation and Handling of Guinea Pigs

The guinea pigs must be quarantined 5 to 7 days prior to the study. The day before the test, the back and hind limbs are shaved taking care not to nick the skin. After shaving, the guinea pigs are fasted, but water is provided.

On the day of the test, the guinea pigs are weighed and identified with an ink mark designating them with numbers 1 through 5 in each group. Groups are formed by random distribution.

Preparation and Route of Administration of Compounds

The oral vehicles are Polyethylene Glycol (PEG 400) (2 ml/kg) and methocel (0.5% w/v) (10 ml/kg). Exposure to the ultrasound of a Branson sonicator assures uniformity of suspension or dissolution of the test compounds. Compounds for parenteral administration are dissolved in saline with the assistance of 0.1N HCl and 0.1N NaOH and then adjusting the pH to near neutrality.

Although test compounds are usually administered orally, other routes of administration such as intravenous, intraperitoneal or subcutaneous may be used.

Preparation of Leukotriene $B_4$ for Intradermal Injection $LTB_4$ is obtained as a stock solution (50 mg/ml) in ethanol and is stored at $-80°$ C. until required for use. The stock solution or an appropriate aliquot is transferred from the ampule into a 10 ml glass vial using a pasteur pipette. The stock solution is then evaporated to dryness under a slow, steady stream of argon gas.

A solution of freshly prepared 0.25% Bovine Albumin in Phosphate-Buffered Saline is bubbled with argon gas until the saturation point is reached (approximately 5 minutes). This argon-saturated vehicle is then used to reconstitute the evaporated $LTB_4$ stock residue to yield a final working concentration of 10 mg/ml. The rubber stoppered vial of $LTB_4$ working solution is kept on wet ice during the study.

Preparation of Evan's Blue Dye Solution

Because Evan's Blue is an easily visible marker that binds to the plasma proteins, it has been selected to assist the investigator in the measurement of the wheals induced during the study. Evan's Blue Dye is dissolved as a 1% w/v solution in 0.9% w/v physiologic saline. The number of 1 ml plastic disposable syringes, fitted with 27 gauge, ½ inch needles and filled with the 1% dye solution, is determined by the number of animals expected to be included in the study.

Conduct of an Experiment

Test compounds or their appropriate controls are administered orally with 16 gauge, 3 inch dosing cannulas. Immediately after dosing, the guinea pig is injected intravenously with 1 ml of 1% Evan's Blue Dye into a digital vein in the left or right shaved hind limb. This injection is facilitated best through the use of a 1 ml plastic syringe fitted with a 27 gauge, ½ inch needle. Immediately following Evan's Blue Injection, the guinea pig is injected intracutaneously at each of 2 sites in the shaved dorsal midline with 0.1 ml of the prepared argon-saturated $LTB_4$ solution (1 mg/0.1 ml). A third site is intracutaneously injected with the argon-saturated 0.25% bovine albumin in phosphate-buffered saline to serve as a vehicle control.

2 hours after challenge, the guinea pigs are euthanized by inhalation of carbon dioxide. Carbon dioxide is administered by inserting a rubber tube from the tank into a plastic bag containing the caged group of guinea pigs. Asphyxiation occurs in approximately 5 minutes.

After death, the dorsal skins are reflected to enable the measurement of 2 perpendicular diameters of the resultant wheals. The area of each wheal is determined using the formula: Area=$\pi r^2$.

Calculations and Statistics

For each guinea pig, the mean of the wheal areas obtained for the 2 injections sites is established after correction is made for the effect of the wheal area induced by the 0.25% Bovine Albumin in Phosphate-Buffered Saline vehicle. Then, a mean area for each treatment group with its corresponding standard error is calculated.

The following equation is used to calculate the percent inhibition of vehicle treated control wheal area by treatment with test compound:

$$\frac{\text{Mean Wheal Area[Control]} - \text{Mean Wheal Area[Treated]}}{\text{Mean Wheal Area[Control]}}$$

In multiple dose experiments, the dose of a test compound that will cause 50% inhibition ($ED_{50}$) can be calculated from the regression equation for the response as percent inhibition (y) and log dose (x) and estimating the ($ED_{50}$) from: $\hat{y}(50)=bx+m$ where:

$\hat{y}$=50% inhibition, x=dose of test compound, b=slope of dose response line and m=intercept of the dose response line.

95% confidence limits of $ED_{50}$ are calculated from the regression equation by the method of Litchfield and Wilcoxon where:

$$ED_{25}=\hat{y}(25)=bx+m,$$

$$ED_{75}=\hat{y}(75)=bx+m \text{ and}$$

$$S=\frac{(ED_{75}/ED_{50}) + (ED_{50}/ED_{25})}{2}$$

where S is the slope function used to compute the limit factor $fED_{50}$ 2.77√N as $fED_{50}$=S. 2.77 is an estimator, N is the square root of the number of animals used for all the doses and $fED_{50}$ is the factor to determine the upper (RU) and lower (RL) limits of the $ED_{50}$ as: RU=$ED_{50}$×$fED_{50}$ and RL=$ED_{50}$+$fED_{50}$. Statistical significance of any inhibition caused by treatment with a test compound can be calculated by applying Student's t (two-tailed) to the data.

Validation and Specificity Studies

The 1 mg/0.1 ml/site challenge dose of $LTB_4$ was selected for the reproducibility, sensitivity and ease of measurement of the resultant wheal. Studies have indicated that size of wheals induced by $LTB_4$ is directly related to the dose administered.

2 hours of incubation after intradermal challenge with $LTB_4$ was selected as the routine timing for the study. Duration studies conducted evidenced the production of measurable, reproducible wheals at the 2 hour endpoint.

In view of the results obtained when compounds of the present invention are subjected to this test, it can be demonstrated that valuable properties as $LTB_4$ antagonists are indicated.

A further test which may be used to determine the ability of compounds of this invention to exhibit $LTB_4$ antagonist activities is as follows:

Guinea Pig Polymorphonuclear Leukocyte Aggregation Assay

Isolation of Guinea Pig PMNS 6 ml of 6% Na-caseinate (in saline) is injected intraperitoneally into 2 male guinea pigs (250–300 g) lightly anesthetized with $CO_2$ or ether. The following day (18–24 hours post injection) the animals are sacrificed by decapitation or $CO_2$ overdose according to the SOP for nonclinical laboratory study methods.

A midline section of abdominal skin is removed and 13 ml Hanks buffer (containing 500 ml 10 mM EDTA/500 ml Hanks) plus 2 ml 7% Na-citrate is injected into the peritoneal cavity. The guinea pig is rocked back and forth 5 times. A small incision is made on the left side of the midline of the abdominal wall (avoid cutting obvious blood vessels). Use a fire-polished pasteur pipette to transfer the buffer plus cells from the abdominal cavity to 2 washed Nalgene (Oak Ridge) centrifuge tubes (half of buffer and cells in each tube). The tubes are then filled to 50 ml with additional citrate-Hanks buffer and centrifuged at 4000 rpm for 10 minutes.

Each pellet is resuspended in 1 ml of citrate-Hanks and then diluted to 50 ml with the same buffer. The cells are incubated for 30 minutes at room temperature on a Hema-Tek aliquot mixer. The cells are filtered through 2 layers of gauze into 50 ml with plastic beakers to remove PMN aggregates and then transferred to fresh, washed, 50 ml Nalgene centrifuge tubes.

The cells are centrifuged for 5 minutes, resuspended in 50 ml of fresh buffer, centrifuged again and then resuspended in 3 ml of citrate-free Hanks buffer. (Following any centrifugation the cells are always resuspended first in 1 ml of the desired fresh buffer.)

An aliquot of the washed cells, diluted 50-fold, is counted, using a microscope and a hemacytometer.

The PMNs are counted as follows:

1. Dilute 50 ml of cells into 450 ml of Hank's buffer.

2. Dilute 50 ml of (1) with 150 ml of Hank's buffer plus 50 ml of Toluidine blue (50x total dilution). Add 10 ml of (2) to the hemacytometer and count cells in 16 large squares (volume counted=1 ml). View the hemacytometer under 40x magnification. The unstained cells are PMNs.

Calculation: assume 149 cells are counted.

$$\frac{\text{\# of cells counted/ml} \times \text{dilution factor} \times 2 \text{ ml}}{\text{desired final cell concentration}} = \text{Final volume of buffer needs/ml of cells}$$

cells/ml = 1,490,000 cells/ml $$\frac{1.49 \times 10^6 \times 50 \times 1}{3 \times 10^7} = \frac{7.45 \times 10^8}{3 \times 10^7} = \frac{2.48 \text{ ml/ml}}{\text{cells counted}}$$

Thus, cells must be diluted 2.48-fold with Hanks buffer (2.48×3=7.44 ml; 7.44− 3.0=4.44; add 4.44 ml buffer to the 3 ml of washed cells). This results in 7.44 ml of cells at a concentration of $3 \times 10^7$ cells per ml.

Instrument Adjustments

Place cuvettes containing $1 \times 10^7$ cells/ml (166 ml PMNs plus 334 ml buffer) plus flea magnets in the aggregometer sample wells. Turn on the Chart Advance to 30 cm/hr. Turn the attenuation dials to mid range and decrease the recorder mV range settings to 50 mV full scale. Press the red "zero" button on the aggregometer and note exactly the position of the recorder pens. Turn the aggregometer left hand "PPP" dials for each cuvette position to the left or right so that the associated recorder pens move to the exact positions noted by pressing the red "zero" button. The electrical circuits are now "balanced". Except for small balance adjustments, do not make any further changes in pen positions by adjusting the "PPP" dials.

Withdraw one of the cuvettes from the aggregometer and note the (positive) direction of recorder pen motion. Replace the cuvette. Using the recorder zero knob, move the recorder pen in the positive direction to the chart paper 95% line. The pens now should not move when the red "zero" button is pressed. The pen also should not move when the mV sensitivity range is changed to 20 or 10 mV full scale (leave at 10 mV).

PMN aggregation should cause the pen to move in the "negative" direction across the chart paper. Make comparable adjustments for the second aggregometer channel but zero the recorder pen on the opposite side of the chart paper. Finally, pressing the zero button on either the recorder or the aggregometer should not cause the pens to move more than a mm or two. This instrument configuration will result in maximal pen deflection following aggregation of cells.

Aggregation Studies

To a cuvette containing 334 ml of buffer and a flea magnet, add 166 ml of PMNs, 10 m of $Ca^{++}/Mg^{++}$ (70/et mM; 1.4/0.7 mM final) and 5 ml of 10 mM cytochalasin-β allow to warm up in the aggregometer (37° C.) for 5 minutes and then add 1 ml of test compound in DMSO or DMSO carrier alone. Note compound effects, if any, for 2 minutes, then add 5 ml of the challenge agonist ($LTB_4$, PAF, etc.) and observe the response for at least 2 minutes. The standard concentrations of agonists used in this assay are arachidonic acid, 6 mM; $LTB_4$, 0.3 nM; PAF, 30 pM; and FMLP, 0.6 nM.

Aggregation is quantitated by measuring, in millimeters, the average maximum deflection of the pen line at 1 minute or less after the addition of $LTB_4$. The maximum response to a control challenge with arachidonic acid may develop somewhat more slowly than this.

Each aggregometer-recorder channel should include its own series of control aggregations. All compounds should be tested at least twice at each concentration of interest. The inhibitory activity observed is expressed as the mean percent change (inhibition) observed relative to the controls determined in that channel. Controls must include appropriate solvent blanks.

The results of the above test demonstrate that compounds within the scope of this invention inhibit the activity of $LTB_4$.

The present Invention also relates to pharmaceutical compositions comprising a product of general formula I, or its salt, optionally combined with any other compatible product, which may be inert or physiologically active. The compounds of the present invention can be administered in composition form to a mammalian host in a variety of forms adapted to the chosen route of administration, i.e., parenteral, oral, rectal or topical. Parenteral administration in this respect includes administration by the following routes: intravenous, intramuscular, subcutaneous, intraocular, intrasynovial, transepthelially Including transdermal, ophthalmic, sublingual and buccal; topically Including ophthalmic, ocular and nasal inhalation via insufflation and aerosol and rectal includes systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers, and the like. By way of solid compositions for oral administration, tablets, pills, powders or granules may be used. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carder. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Compositions for parenteral administration may be aqueous or non-aqueous sterile solutions, suspensions or emulsions. Solutions of the active compound as a free base or pharmacologically acceptable salt can be prepared in water suitably mixed with a surfactant such as hydroxypropylcellulose. By way of solvent or medium, propylene glycol, polyethylene glycol, vegetable oils, in particular olive oil, and injectable organic esters, for example ethyl oleate may be used. These compositions may also contain adjuvants, in particular wetting, emulsifying or dispersing agents. Dispersion can also be prepared in glycerol, liquid polyethylene glycols, and mixtures thereof and in oils. Under ordinary conditions of storage and use, these preparations contain a preservative to prevent the growth of microorganisms. Sterilization may be performed in several ways, for example by means of a bacteriological filter, by incorporating sterilizing agents into the composition, by irradiation or by heating. They may also be prepared in the form of sterile solid compositions to be dissolved at the time of use in sterile water or any other injectable sterile medium.

Compositions for rectal administration are suppositories or rectal capsules which may contain, in addition to the active product, excipients such as cacao butter or Suppocire. Compositions for topical administration may be for example creams, pomades or lotions.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other Ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

In human therapy, the products according to the invention may be particularly useful in the treatment of diseases of inflammatory origin. They may therefore prove very useful in osteoarticulatory pathology in the treatment of arthritis, rheumatoid polyarthritis, spondylarthritis, gout, arthrosis, chondrocalcinosis, as well as in other inflammatory pathologies affecting the lungs, the digestive tracts (ulcerous colitis, hepatic inflammation, cirrhosis, diseases of the colon, Crohn's disease), the skin (psoriasis, herpes, acne, erythema, eczema, dermatitis), the eyes, the nasal tracts, the buccal cavity and the teeth. They may also be used in the treatment of nasal and bronchial allergies (asthma). The products according to the invention may also be useful in the treatment of inflammations connected with the fitting of implants, by improving their compatibility with the surrounding tissue. They may also play a role in immunoregulation (auto-immune diseases), ischemia and reperfusion (cardiac in particular). These products may also exert a beneficial effect in the treatment of hyperthermia and pain.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration. Generally, the physician will determine the dose he judges most suitable depending on the age, the weight and the other factors specific to the individual under treatment.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The following examples illustrate the compositions according to the invention.

EXAMPLE A

Tablets of the active product having the following composition are prepared according to the usual technique:

| | |
|---|---|
| 2,2-Dimethyl-6-[(4,6-diphenyl-2-pyridyl)oxy] hexanoic acid | 100 mg |
| starch | 332 mg |
| silica | 120 mg |
| magnesium stearate | 12 mg |

EXAMPLE B

Tablets of the active product having the following composition are prepared according to the usual technique:

| | |
|---|---|
| 5-(2,2-Dimethyl-5-[(4,6-diphenyl-2-pyridyl)-oxy]pentyl}[1H]-tetrazole | 100 mg |
| starch | 332 mg |
| silica | 120 mg |
| magnesium stearate | 12 mg |

We claim:

1. A compound of the formula:

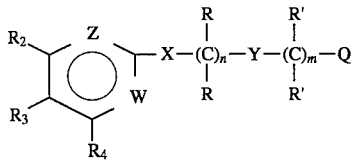

where m is 1–8, n is 0–8 and n+m is 2–8;

X is S, O, NR', CR'R', CR'=CR', CO—NR", NR"—CO, CHR'—O or a bond;

Y is S, O, NR", CR'R', CR'=CR', CO—NR', NR"—CO, CO or CR'—OH;

W is CR';

Z is N;

R and R' are independently hydrogen or alkyl;

R" is hydrogen;

$R_1$ is phenyl, substituted phenyl or thienyl where the substituents are selected from alkyl, alkoxy, halo, haloalkyl, alkylthio, nitro, amine and mono- or dialkylamino;

$R_2$ and $R_3$ together with the ring to which they are attached form an optionally substituted fused bicyclic ring system where the substituents are selected from alkyl, alkoxy or halo;

$R_4$ is $R_1$, $R_1$-loweralkyl- or $X_1$—$(CH_2)_t$—$R_1$— where $X_1$ is S, O, NR", CR'R' or CO and t is 1–4; and Q is $COOR_6$, COOM, $CONR_7R_7$, CN, $CONHSO_2R_6$, tetrazolyl or tetrazolyl substituted with alkyl, carboxyalkyl or carbalkoxyalkyl and

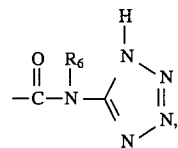

where $R_6$ is hydrogen, alkyl or aralkyl, $R_7$ is hydrogen, alkyl, aralkyl or cycloalkyl and M is a metal or ammonia salt; or a pharmaceutically acceptable salt thereof.

2. A compound according to claim 1 where m is 1–8 and n is 0–8; and n+m is 2–8;

X is S, O, NR", CR'R' or a bond;

Y is S, O, NR" or CR'R';

W is CR';

Z is N;

R and R' are independently hydrogen or alkyl;

$R_2$ and $R_3$ together with the ring to which they are attached form an optionally substituted fused bicyclic ring which may further be substituted with halo, alkyl or alkoxy;

$R_4$ is phenyl or substituted phenyl and may be substituted with 1–2 substituents independently selected from alkyl, alkoxy, halo, trifluoromethyl, nitro, amino, and mono- or dialkylamino; and Q is $COOR_6$, COONa, $CONR_7R_7$, or tetrazolyl where $R_6$ and $R_7$ are independently hydrogen or alkyl.

3. A compound according to claim 2 where

X is S, O, NR"; and

Y is O or CR'R'.

4. A compound according to claim 2 where

X is a bond; and

Y is S, O, NR".

5. A compound according to claim 2 where

X is a bond; and

Y is CR'R'.

6. A compound according to claim 2 where

X is CR'R'; and

Y is CR'R'.

7. A pharmaceutical composition for use in the treatment of an inflammatory disorder involving $LTB_4$ agonist-mediated activity which composition comprises a compound according to claim 1 in an amount effective to inhibit and/or decrease inflammation, in combination with a pharmaceutically acceptable diluent or adjuvant.

8. A method for the treatment of inflammatory diseases caused by tissue degrading enzymes and reactive chemicals liberated by tissue-infiltrating and aggregating polymorphonuclear leukocytes in humans and mammals comprising administering thereto an effective amount of a compound of the formula according to claim 1.

9. A method for the treatment of an inflammatory disorder in humans and other mammals comprising administering thereto an effective amount to inhibit and/or decrease inflammation of a compound of the formula according to claim 1.

* * * * *